(12) United States Patent
Shiraishi

(10) Patent No.: US 12,136,258 B2
(45) Date of Patent: Nov. 5, 2024

(54) INFORMATION PROCESSING APPARATUS, METHOD FOR OPERATING INFORMATION PROCESSING APPARATUS, AND OPERATING PROGRAM OF INFORMATION PROCESSING APPARATUS

(71) Applicant: FUJIFILM CORPORATION, Tokyo (JP)

(72) Inventor: Yasushi Shiraishi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 322 days.

(21) Appl. No.: 17/683,259

(22) Filed: Feb. 28, 2022

(65) Prior Publication Data
US 2022/0189149 A1    Jun. 16, 2022

Related U.S. Application Data

(63) Continuation of application No. PCT/JP2020/017405, filed on Apr. 22, 2020.

(30) Foreign Application Priority Data

Sep. 27, 2019   (JP) .................. 2019-177219

(51) Int. Cl.
*G06K 9/00* (2022.01)
*G06V 10/10* (2022.01)
(Continued)

(52) U.S. Cl.
CPC ............ *G06V 10/776* (2022.01); *G06V 10/16* (2022.01); *G06V 10/26* (2022.01); *G06V 10/764* (2022.01);
(Continued)

(58) Field of Classification Search
CPC ...... G06V 10/776; G06V 10/16; G06V 10/26; G06V 10/764; G06V 10/774;
(Continued)

(56) References Cited

U.S. PATENT DOCUMENTS 8,442,309 B2 * 5/2013 Ranganathan ....... G06V 10/764
707/999.005
8,675,105 B2 * 3/2014 Lansel ................ H04N 25/134
382/280
(Continued)

FOREIGN PATENT DOCUMENTS

| CN | 107563383 A | * | 1/2018 | |
| CN | 107832680 A | * | 3/2018 | ......... G06F 16/5854 |

(Continued)

OTHER PUBLICATIONS

Bikhet, Sawsan F. et al. "Segentation and Classification of White Blood Cells", 2000 IEEE International Conference on Acoustics, Speech, and Signal Processing, Proceedings, Istanbul, Turkey, Jun. 5-9, 2000, New York, US, Jun. 5, 2000, pp. 2259-2261.
(Continued)

*Primary Examiner* — Shervin K Nakhjavan
(74) *Attorney, Agent, or Firm* — SOLARIS Intellectual Property Group, PLLC

(57) ABSTRACT

An information processing apparatus includes an acquisition unit that acquires an output image output from a trained model as a result of causing the trained model to perform semantic segmentation in which discrimination of a class which is a type of an object appearing in an input image is performed on a pixel-by-pixel basis, an evaluation unit that evaluates validity of the semantic segmentation based on the output image, and a display controller that performs control such that an evaluation result indicating that the semantic segmentation does not have validity is displayed in a case
(Continued)

where the evaluation unit evaluates that the semantic segmentation does not have validity.

12 Claims, 22 Drawing Sheets

(51) Int. Cl.
  *G06V 10/26* (2022.01)
  *G06V 10/764* (2022.01)
  *G06V 10/774* (2022.01)
  *G06V 10/776* (2022.01)
  *G06V 20/69* (2022.01)

(52) U.S. Cl.
  CPC .......... *G06V 10/774* (2022.01); *G06V 20/695* (2022.01); *G06V 20/698* (2022.01)

(58) Field of Classification Search
  CPC .... G06V 20/695; G06V 20/698; G06V 20/13; G06V 10/82; G06V 10/22; G06V 10/25; G06V 10/98; C12M 1/34; C12Q 1/04; G06T 7/00
  See application file for complete search history.

(56) References Cited

U.S. PATENT DOCUMENTS

| | | | | |
|---|---|---|---|---|
| 10,360,999 | B2* | 7/2019 | Bernard | A61B 8/5223 |
| 10,818,386 | B2* | 10/2020 | Yao | H04L 67/01 |
| 2016/0259963 | A1 | 9/2016 | Cohen et al. | |
| 2018/0165509 | A1 | 6/2018 | Cohen et al. | |
| 2019/0295260 | A1 | 9/2019 | Mehta et al. | |
| 2020/0125894 | A1 | 4/2020 | Maeda et al. | |
| 2021/0342569 | A1* | 11/2021 | Sieckmann | G06V 20/693 |

FOREIGN PATENT DOCUMENTS

| | | | | | |
|---|---|---|---|---|---|
| CN | 109145939 | A | * | 1/2019 | ........... G06K 9/6267 |
| CN | 109598727 | A | * | 4/2019 | ........... G06K 9/6273 |
| CN | 110490081 | A | * | 11/2019 | ........... G06K 9/0063 |
| CN | 110689623 | B | * | 12/2020 | ......... G06K 9/00671 |
| EP | 3761230 | A1 | * | 1/2021 | ............. G06K 9/033 |
| JP | 2006-349533 | A | | 12/2006 | |
| JP | 2016-534709 | A | | 11/2016 | |
| WO | 2015065697 | A1 | | 5/2015 | |
| WO | 2017051195 | A1 | | 3/2017 | |
| WO | 2018/189875 | A1 | | 10/2018 | |
| WO | WO-2018222755 | A1 | * | 12/2018 | ............. A61B 5/055 |

OTHER PUBLICATIONS

Ionita, Marius G. et al., "Automatic periodic noise removal in microscopy images", International Symposium on Signals, Circuits and Systems, Jul. 13, 2017, pp. 1-4.
Falk, Thorsten et al., "U-Net: deep learning for cell counting, detection, and morphometry," Nature Methods, Nature Publishing Group, New York, vol. 16, No. 1, Dec. 17, 2018, pp. 67-70.
Extended European Search Report dated Oct. 10, 2022, issued in corresponding EP Patent Application No. 20869859.7.
International Search Report issued in International Application No. PCT/JP2020/017405 on Jul. 28, 2020.
Written Opinion of the ISA issued in International Application No. PCT/JP2020/017405 on Jul. 28, 2020.
English language translation of the following: Office action dated Dec. 6, 2022 from the JPO in a Japanese patent application No. 2021-548317 corresponding to the instant patent application.
Office Action dated Jun. 26, 2024, issued by the EPO in corresponding EP Patent Application No. 20869859.7.

* cited by examiner

FIG. 15

| TYPE OF CELL | THRESHOLD VALUE TO BE COMPARED WITH AREA RATIO |
|---|---|
| NERVE CELL | 0.3 TO 0.5 |
| MYOCARDIAL CELL | 0.2 TO 0.5 |
| HEPATOCYTE | 0.4 TO 0.6 |
| ⋮ | ⋮ |

FIG. 16

| NUMBER OF CULTURE DAYS OF CELL | THRESHOLD VALUE TO BE COMPARED WITH AREA RATIO |
|---|---|
| FIRST DAY | 0.1 TO 0.3 |
| SECOND DAY | 0.2 TO 0.4 |
| THIRD DAY | 0.3 TO 0.5 |
| ⋮ | ⋮ |

FIG. 17

| TYPE OF CELL | NUMBER OF CULTURE DAYS OF CELL | THRESHOLD VALUE TO BE COMPARED WITH AREA RATIO ~87 |
|---|---|---|
| NERVE CELL | FIRST DAY | 0.2 TO 0.3 |
| | SECOND DAY | 0.22 TO 0.33 |
| | THIRD DAY | 0.24 TO 0.38 |
| | ⋮ | ⋮ |
| MYOCARDIAL CELL | FIRST DAY | 0.2 TO 0.25 |
| | ⋮ | ⋮ |
| HEPATOCYTE | FIRST DAY | 0.35 TO 0.55 |
| | ⋮ | ⋮ |
| ⋮ | ⋮ | ⋮ |

INFORMATION PROCESSING APPARATUS, METHOD FOR OPERATING INFORMATION PROCESSING APPARATUS, AND OPERATING PROGRAM OF INFORMATION PROCESSING APPARATUS

CROSS-REFERENCE TO RELATED APPLICATIONS

This application is a continuation application of International Application No. PCT/JP2020/017405 filed on Apr. 22, 2020, the disclosure of which is incorporated herein by reference in its entirety. Further, this application claims priority from Japanese Patent Application No. 2019-177219 filed on Sep. 27, 2019, the disclosure of which is incorporated herein by reference in its entirety.

BACKGROUND

1. Technical Field

A disclosed technology relates to an information processing apparatus, a method for operating an information processing apparatus, and an operating program of an information processing apparatus.

2. Description of the Related Art

A trained model is caused to perform semantic segmentation in which discrimination of a class which is a type of an object appearing in an input image is performed on a pixel-by-pixel basis and to output an output image in which the discriminated class is classified by color or the like from the trained model. Statistical information such as the number of objects appearing in the input image is derived based on the output image.

JP2016-534709A describes a technology for giving, as an input image, a cell image obtained by imaging a plurality of cells in culture to a trained model for performing semantic segmentation. In JP2016-534709A, the trained model is caused to discriminate the cell as a class. The number and size of cells are derived as statistical information based on the output image. The output image and the statistical information are output.

SUMMARY

The discrimination accuracy of the class of the semantic segmentation by the trained model is not 100%, and the class may be erroneously discriminated. However, a user tends to focus on the statistical information of the output image and the statistical information, and may not check the output image on which the statistical information is based in order to confirm the validity of the semantic segmentation. Thus, there is a concern that the user overlooks that the semantic segmentation by the trained model does not have validity.

It is an object of the disclosed technology to provide an information processing apparatus, a method for operating an information processing apparatus, and an operating program of an information processing apparatus capable of reliably notifying that semantic segmentation by a trained model does not have validity.

In order to achieve the above object, an information processing apparatus according to the present disclosure includes an acquisition unit that acquires an output image output from a trained model as a result of causing the trained model to perform semantic segmentation in which discrimination of a class which is a type of an object appearing in an input image is performed on a pixel-by-pixel basis, an evaluation unit that evaluates validity of the semantic segmentation based on the output image, and a display controller that performs control such that an evaluation result indicating that the semantic segmentation does not have validity is displayed in a case where the evaluation unit evaluates that the semantic segmentation does not have validity.

It is preferable that the evaluation unit calculates an image feature value from the output image and evaluates the validity of the semantic segmentation by using the image feature value.

It is preferable that the input image is an image obtained by imaging one region of a plurality of regions obtained by dividing an imaging target, and the evaluation unit generates an entire image indicating the entire imaging target by joining a plurality of the output images corresponding to a plurality of the input images imaged for the plurality of regions, and calculates, as the image feature value, an intensity of a periodic noise of the entire image which is caused by dividing the imaging target into the plurality of regions and imaging the divided regions.

It is preferable that the information processing apparatus further includes a derivation unit that derives statistical information of the object appearing in the input image based on the output image, and the display controller performs control such that a warning indicating that reliability of the statistical information is low is displayed together with the evaluation result in a case where the evaluation unit evaluates that the semantic segmentation does not have validity.

It is preferable that the information processing apparatus further includes an output controller that performs control such that the output image evaluated as having no validity of the semantic segmentation is output.

It is preferable that the information processing apparatus further includes an acceptance unit that accepts a correction instruction for the class of the output image evaluated as having no validity of the semantic segmentation.

It is preferable that the information processing apparatus further includes a correction unit that corrects the class of the output image evaluated as having no validity of the semantic segmentation.

It is preferable that the information processing apparatus further includes a re-learning unit that re-trains the trained model by using, as learning data, a corrected output image obtained by correcting the class of the output image evaluated as having no validity of the semantic segmentation.

It is preferable that the input image is a cell image obtained by imaging a plurality of cells in culture.

It is preferable that the evaluation unit calculates, as the image feature value, an area ratio between at least two types of classes including the cell or a structure of the cell.

It is preferable that the evaluation unit changes a threshold value used for evaluating the validity of the semantic segmentation in comparison with the area ratio according to a type of the cell and/or the number of culture days of the cell.

A method for operating an information processing apparatus according to the present disclosure includes an acquisition step of acquiring an output image output from a trained model as a result of causing the trained model to perform semantic segmentation in which discrimination of a class which is a type of an object appearing in an input image is performed on a pixel-by-pixel basis, an evaluation step of evaluating validity of the semantic segmentation based on the output image, and a display control step of performing control such that an evaluation result indicating that the semantic segmentation does not have validity is displayed in a case where the semantic segmentation is evaluated as having no validity in the evaluation step.

An operating program of an information processing apparatus according to the present disclosure causes a computer to function as an acquisition unit that acquires an output image output from a trained model as a result of causing the trained model to perform semantic segmentation in which discrimination of a class which is a type of an object appearing in an input image is performed on a pixel-by-pixel basis, an evaluation unit that evaluates validity of the semantic segmentation based on the output image, and a display controller that performs control such that an evaluation result indicating that the semantic segmentation does not have validity is displayed in a case where the evaluation unit evaluates that the semantic segmentation does not have validity.

According to the disclosed technology, it is possible to provide an information processing apparatus, a method for operating an information processing apparatus, and an operating program of an information processing apparatus capable of surely notifying that semantic segmentation by a trained model does not have validity.

BRIEF DESCRIPTION OF THE DRAWINGS

Exemplary embodiments according to the technique of the present disclosure will be described in detail based on the following figures, wherein:

FIG. 1 is a diagram illustrating an information processing apparatus and the like;

FIG. 15 is a diagram illustrating an example in which a threshold value to be compared with an area ratio obtained by dividing an area of a cell nucleus by an area of a cellular cytoplasm changes according to a type of a cell;

FIG. 16 is a diagram illustrating an example in which the threshold value to be compared with the area ratio obtained by dividing the area of the cell nucleus by the area of the cellular cytoplasm changes according to the number of culture days of the cell;

FIG. 17 is a diagram illustrating an example in which the threshold value to be compared with the area ratio obtained by dividing the area of the cell nucleus by the area of the cellular cytoplasm changes according to the type and the number of culture days of the cell;

DETAILED DESCRIPTION

First Embodiment

Figure 1:
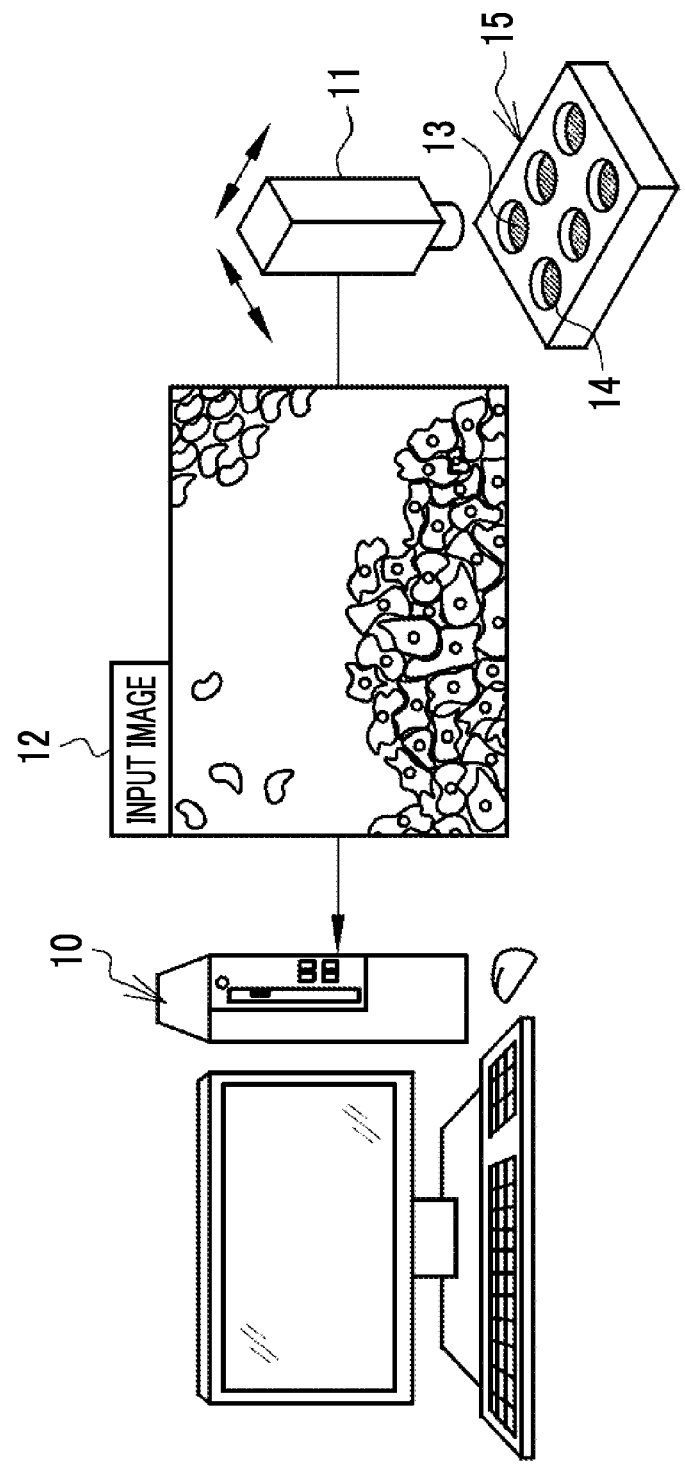

In FIG. 1, an information processing apparatus 10 is, for example, a desktop personal computer, and receives an input image 12 imaged by an imaging device 11. The imaging device 11 is, for example, a phase-contrast microscope, a bright-field microscope, or the like. A well plate 15 in which a plurality of wells 14 for culturing cells 13 (see also FIGS. 5 and 6) are formed is set in the imaging device 11. The imaging device 11 images a cell image obtained by imaging a plurality of cells 13 in culture as the input image 12.

Figure 2:
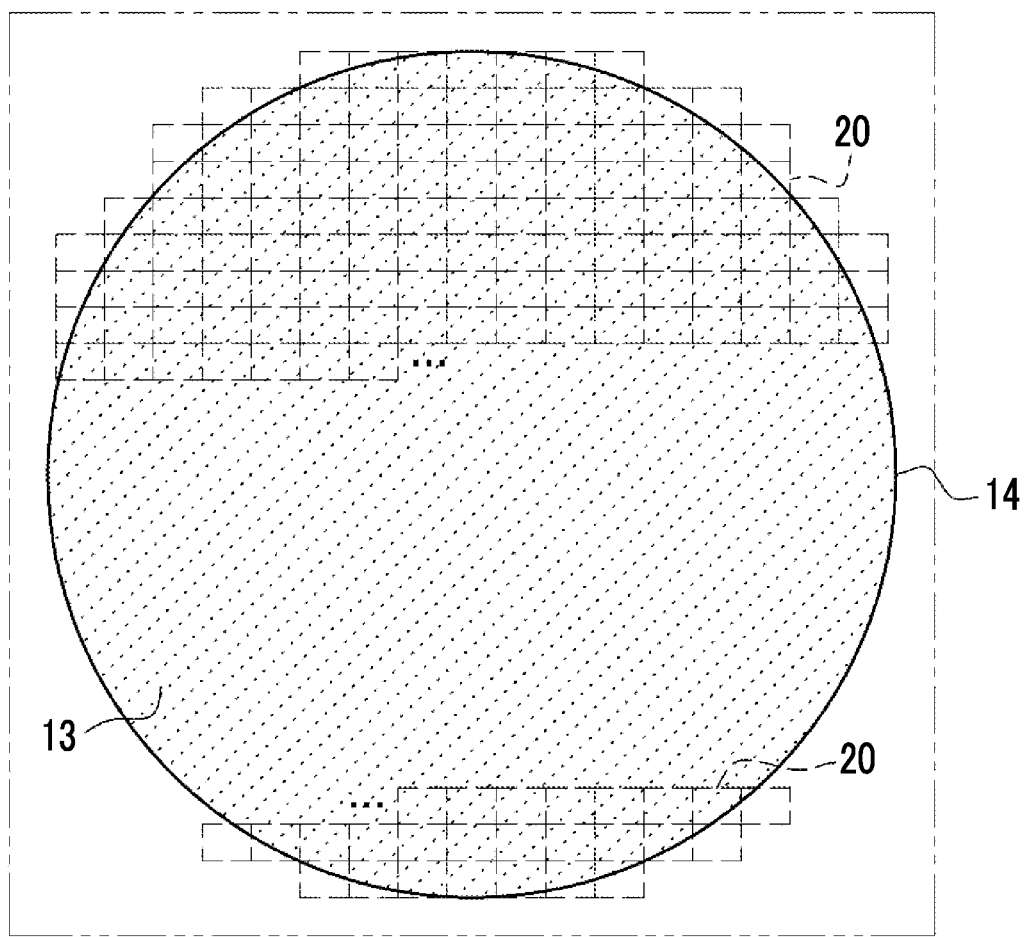
FIG. 2 is a diagram illustrating a plurality of regions in which a well is divided.

As illustrated in FIG. 2, the imaging device 11 images the input image 12 for each of a plurality of regions 20 in which the well 14 is divided. Thus, as illustrated by arrows in FIG. 1, the imaging device 11 can move in two directions orthogonal to each other. The number of the plurality of regions 20 is, for example, several thousand. The well 14 is an example of an "imaging target" according to a disclosed technology.

Figure 3:
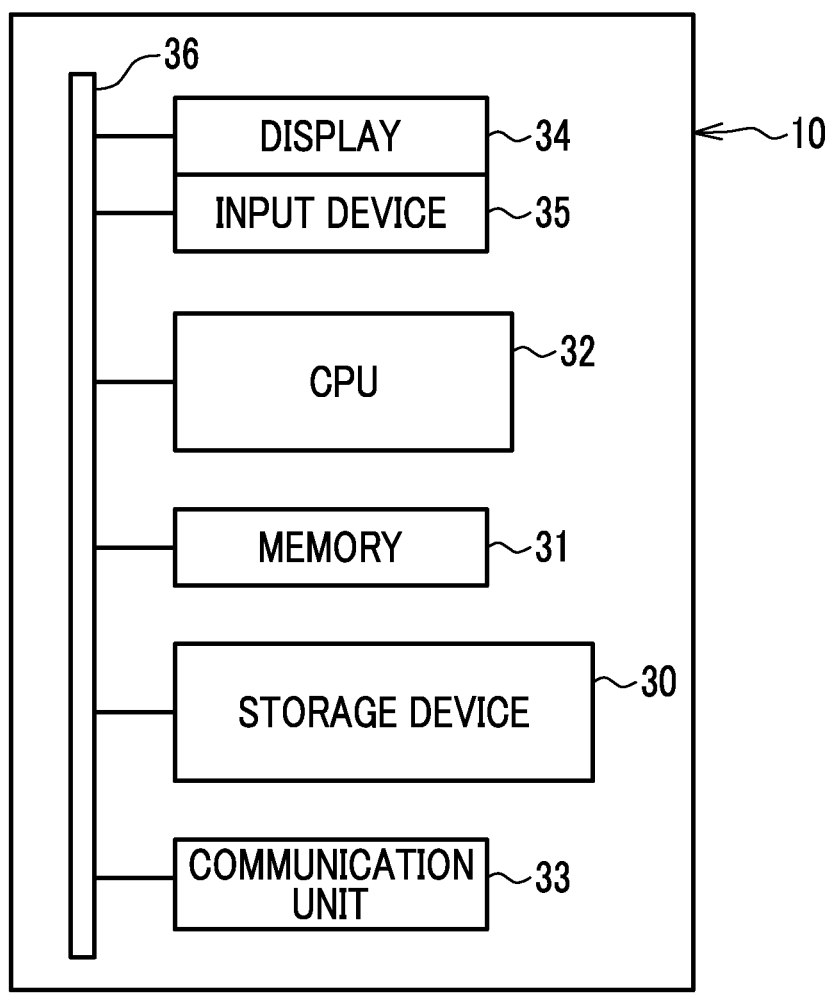
FIG. 3 is a block diagram illustrating a computer constituting the information processing apparatus.

In FIG. 3, the computer constituting the information processing apparatus 10 includes a storage device 30, a memory 31, a central processing unit (CPU) 32, a communication unit 33, a display 34, and an input device 35. These components are interconnected via a busline 36.

The storage device 30 is a hard disk drive built in the computer constituting the information processing apparatus 10 or connected via a cable or a network. Alternatively, the storage device 30 is a disk array in which a plurality of hard disk drives are connected in series. The storage device 30 stores control programs such as an operating system, various application programs, and various kinds of data attached to these programs. A solid state drive may be used instead of the hard disk drive.

The memory 31 is a work memory for the CPU 32 to execute processing. The CPU 32 comprehensively controls the units of the computer by loading the program stored in the storage device 30 into the memory 31 and executing the processing according to the program.

The communication unit 33 is a network interface that controls transmission of various kinds of information via a network such as a local area network (LAN). The display 34 displays various screens. The computer constituting the information processing apparatus 10 accepts an input of an operation instruction from the input device 35 through various screens. The input device 35 is a keyboard, a mouse, a touch panel, or the like.

Figure 4:
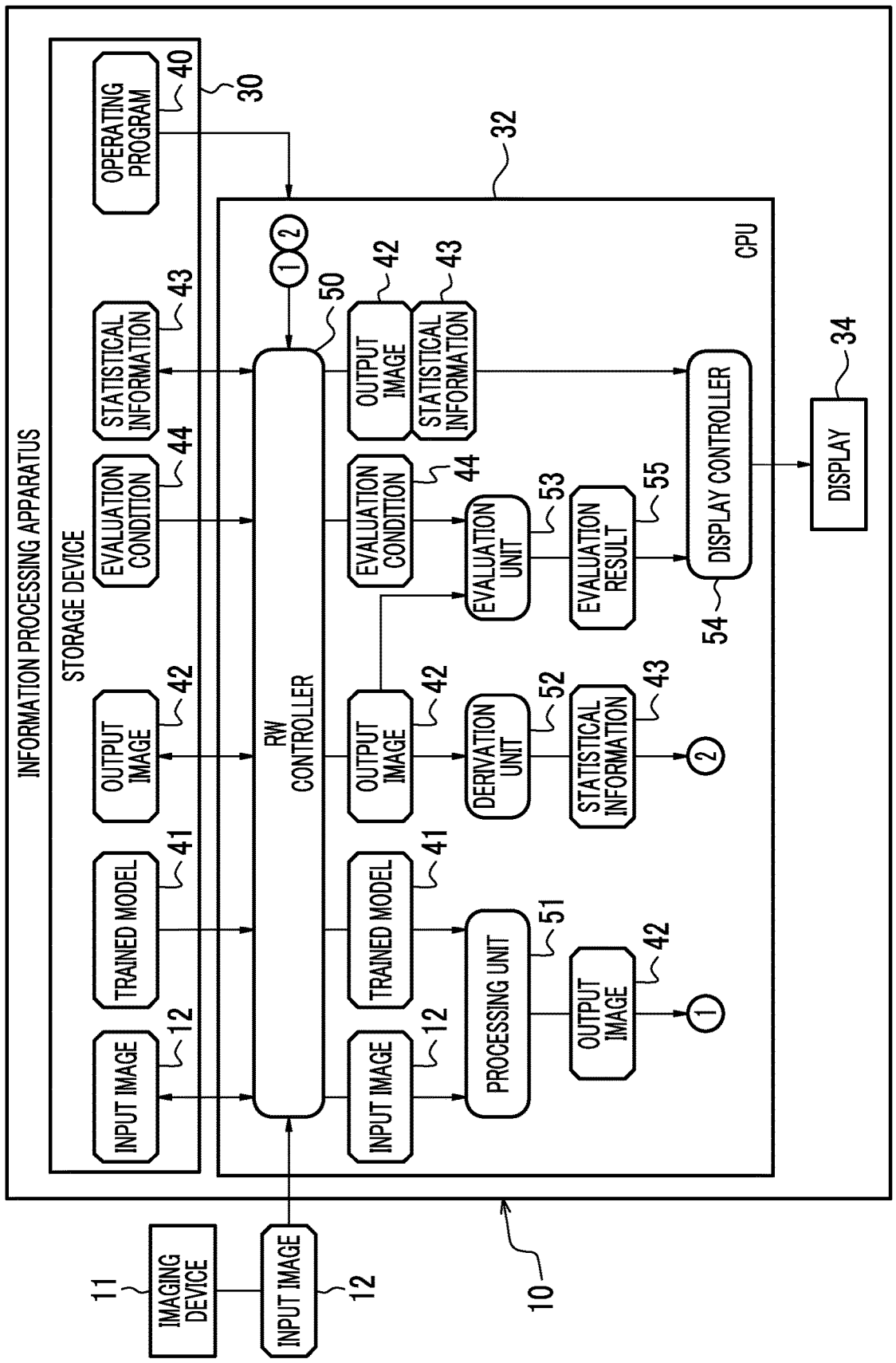
FIG. 4 is a block diagram illustrating a processing unit of a CPU of the information processing apparatus.

In FIG. 4, an operating program 40 is stored in the storage device 30 of the information processing apparatus 10. The operating program 40 is an application program for causing the computer to function as the information processing apparatus 10. That is, the operating program 40 is an example of an "operating program of an information processing apparatus" according to the disclosed technology. The storage device 30 also stores the input image 12, a trained model 41, an output image 42, statistical information 43, and an evaluation condition 44.

In a case where the operating program 40 is activated, the CPU 32 of the computer constituting the information processing apparatus 10 functions as a read write (hereinafter, abbreviated as RW) controller 50, a processing unit 51, a derivation unit 52, an evaluation unit 53, and a display controller 54 in cooperation with the memory 31 and the like.

The RW controller 50 performs control such that various kinds of data are stored in the storage device 30 and various kinds of data within the storage device 30 are read out. For example, the RW controller 50 receives the input image 12 from the imaging device 11 and stores the input image in the storage device 30. The RW controller 50 reads out the input image 12 and the trained model 41 from the storage device 30, and outputs the input image and the trained model to the processing unit 51.

The processing unit 51 gives the input image 12 to the trained model 41. The trained model 41 is caused to perform semantic segmentation for discriminating a class which is a type of an object appearing in the input image 12 on a pixel-by-pixel basis, and the trained model 41 is caused to output the output image 42. The processing unit 51 passes the output image 42 to the RW controller 50. The RW controller 50 stores the output image 42 in the storage device 30. The trained model 41 is, for example, a convolutional neural network such as a U-shaped neural network (U-Net), SegNet, and a residual network (ResNet).

The RW controller 50 reads out the output image 42 from the storage device 30 and outputs the output image to the derivation unit 52 and the evaluation unit 53. That is, the RW controller 50 is an example of an "acquisition unit" according to the disclosed technology.

The RW controller 50 reads out the evaluation condition 44 from the storage device 30 and outputs the evaluation condition to the evaluation unit 53.

The derivation unit 52 derives the statistical information 43 of the cell 13 based on the output image 42. The derivation unit 52 outputs the statistical information 43 to the RW controller 50. The RW controller 50 stores the statistical information 43 in the storage device 30.

The evaluation unit 53 evaluates the validity of the semantic segmentation by the trained model 41 based on the output image 42 and the evaluation condition 44. The evaluation unit 53 outputs an evaluation result 55 of the validity to the display controller 54.

The RW controller 50 reads out the output image 42 and the statistical information 43 from the storage device 30 and outputs the output image and the statistical information to the display controller 54.

The display controller 54 controls the display of various screens on the display 34. The various screens include an analysis result display screen 70 (see FIGS. 11 and 12) which is a screen for displaying the output image 42 and the statistical information 43, an evaluation result display screen 80 which is a screen for displaying the evaluation result 55 of the evaluation unit 53 (see FIG. 12), and the like.

Figure 5:
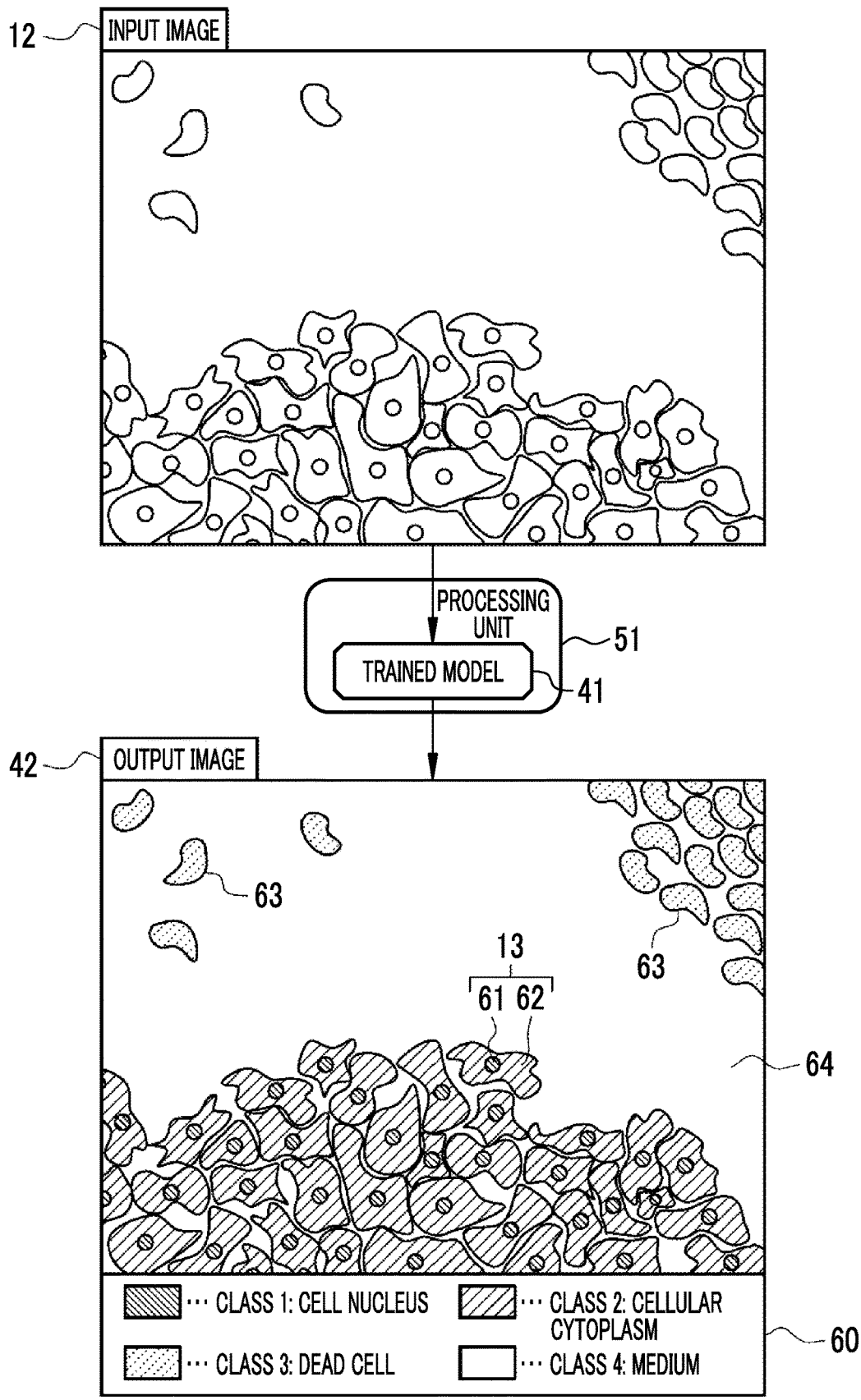
FIG. 5 is a diagram illustrating an example of an input image and an output image.
Figure 6:
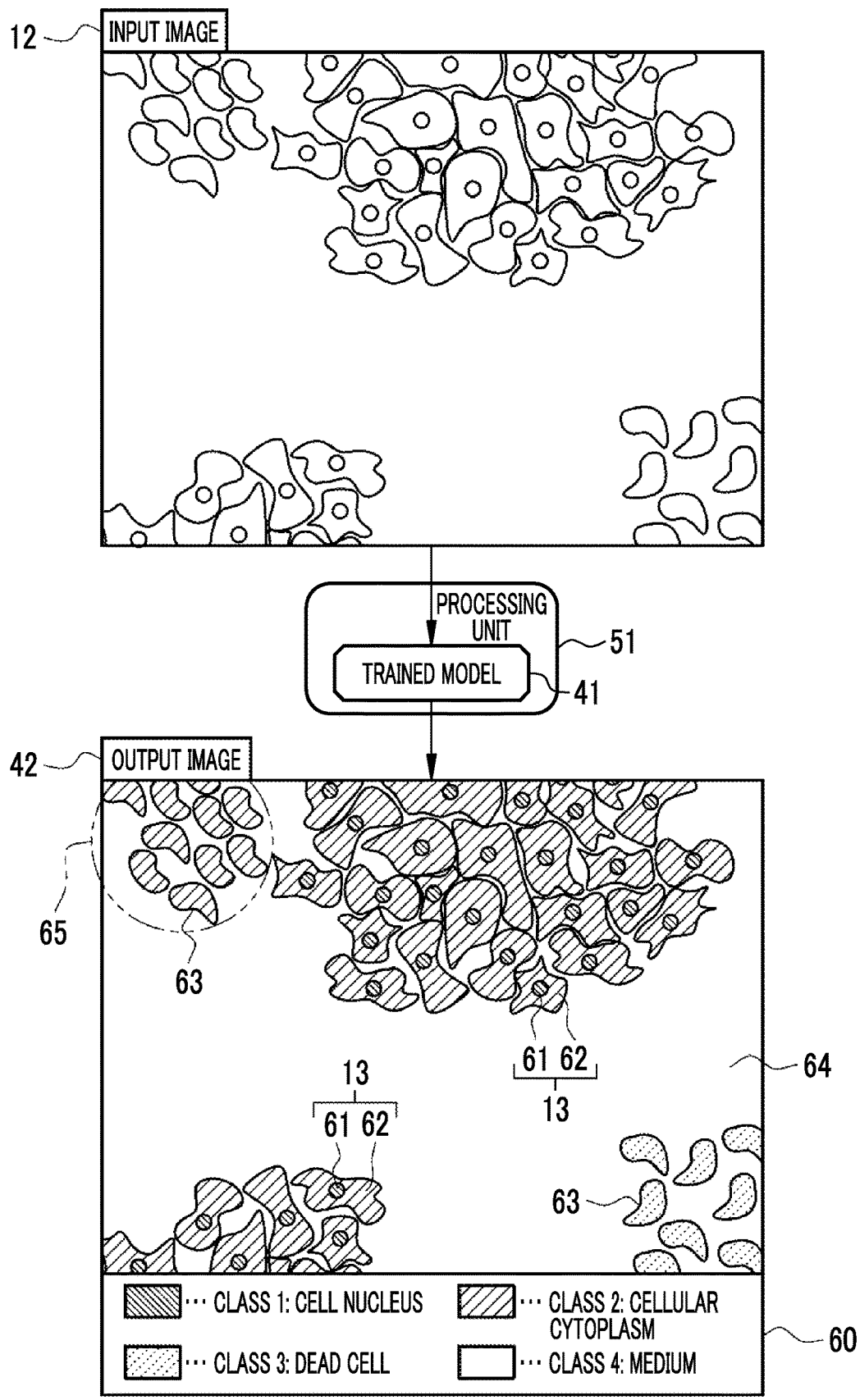
FIG. 6 is a diagram illustrating an example of the input image and the output image.

In FIGS. 5 and 6, as illustrated in an explanatory note 60, the output image 42 is an image obtained by discriminating a cell nucleus 61 of class 1, a cellular cytoplasm 62 of class 2, a dead cell 63 of class 3, and a medium 64 of class 4 and color-coding these classes. The cell 13 is constituted by the cell nucleus 61 and the cellular cytoplasm 62. The cell nucleus 61, the cellular cytoplasm 62, the dead cell 63, and the medium 64 are examples of an "object" according to the disclosed technology.

FIG. 5 shows a case where the discrimination of the class of the semantic segmentation by the trained model 41 is correct. On the other hand, FIG. 6 shows a case where the discrimination of the class of the semantic segmentation by the trained model 41 is incorrect. Specifically, as illustrated in a circle 65 of a dashed double-dotted line, the dead cell 63 to be discriminated as class 3 is erroneously discriminated as the cellular cytoplasm 62 of class 2. Although not illustrated, in the trained model 41, a periodic noise caused by dividing the well 14 into the plurality of regions 20 and imaging the divided regions may be erroneously discriminated as the cell nucleus 61 of class 1 or the cellular cytoplasm 62 of class 2. Such the erroneous discrimination of the class of the semantic segmentation by the trained model 41 often occurs in a case where the input image 12 of the type not given as learning data is input in a training phase of the trained model 41. As described above, the trained model 41 may erroneously discriminate the class of the semantic segmentation.

Figure 7:
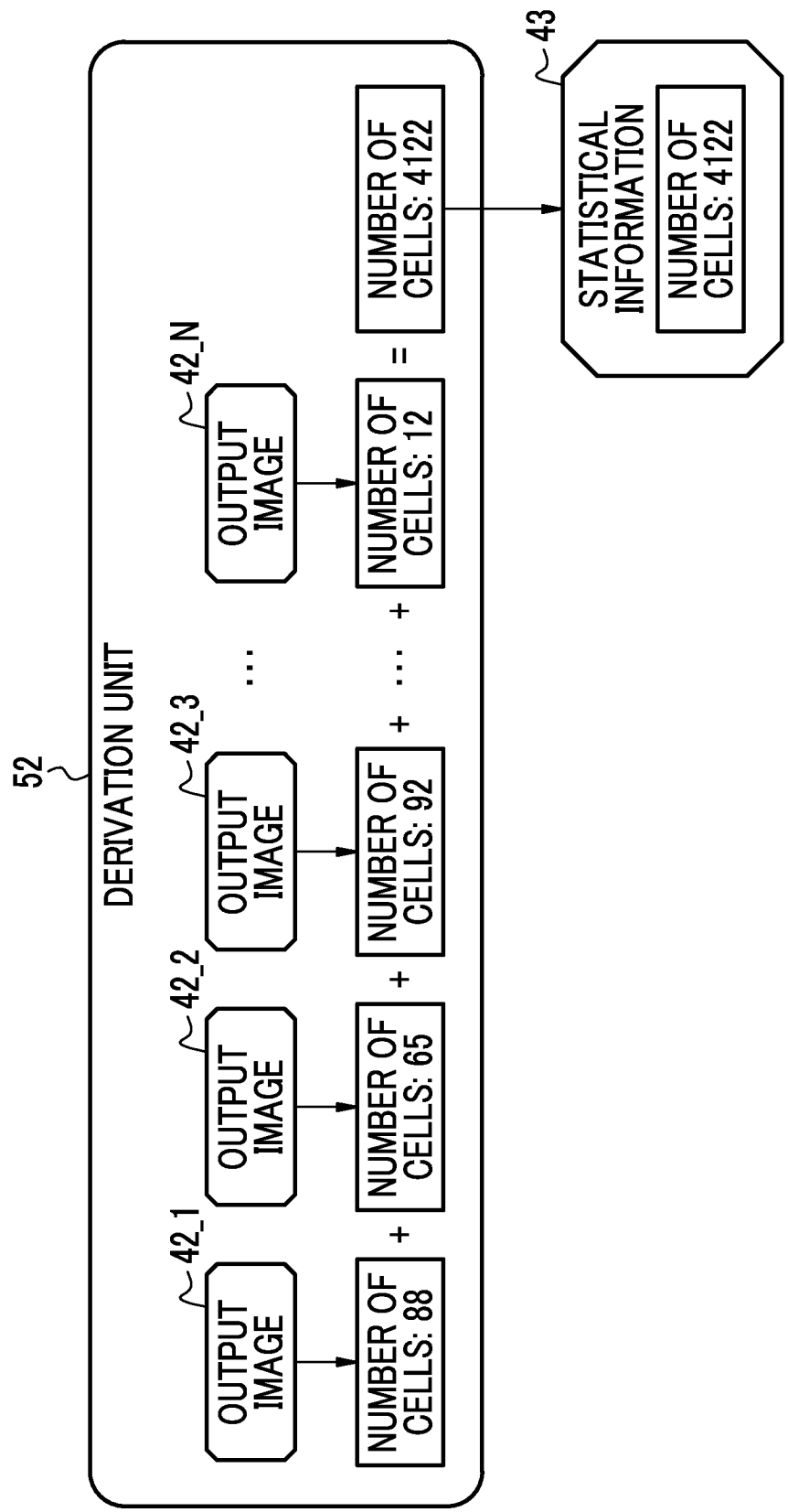
FIG. 7 is a diagram illustrating processing of a derivation unit.

As illustrated in FIG. 7, the derivation unit 52 counts the number of cells 13 (hereinafter, referred to as the number of cells) for each of a plurality of output images 42_1, 42_2, 42_3, . . . , and 42_N corresponding to the plurality of input images 12 for the plurality of regions 20 illustrated in FIG. 2. For example, the derivation unit 52 counts the number of cells appearing in each of the output images 42_1 to 42_N by counting the number of cell nucleuses 61. The derivation unit 52 outputs, as the statistical information 43, the total number of cells appearing in each of the output images 42_1 to 42_N. N is a natural number representing the total number of output images 42.

Figure 8:
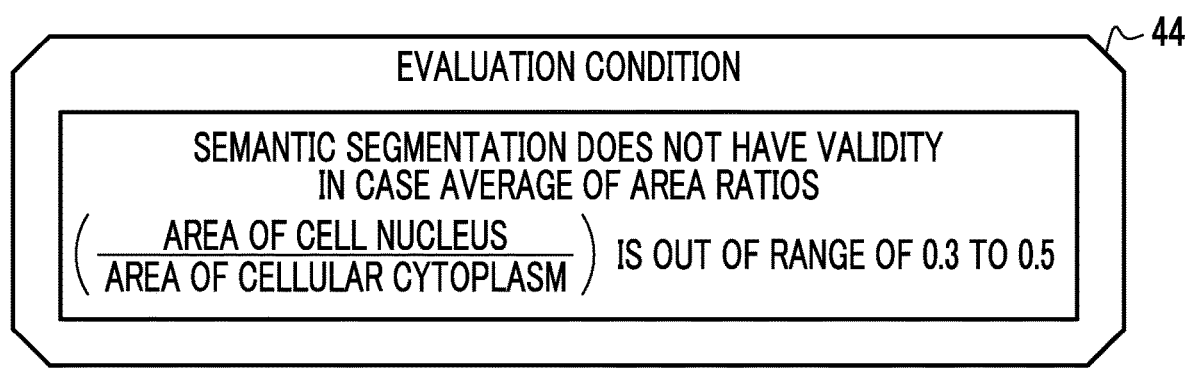
FIG. 8 is a diagram illustrating an evaluation condition.

In FIG. 8, the evaluation condition 44 is a content indicating that the semantic segmentation by the trained model 41 is evaluated as having no validity in a case where an average of area ratios obtained by dividing an area of the cell nucleus 61 by an area of the cellular cytoplasm 62 (area of cell nucleus 61/area of cellular cytoplasm 62) is out of a range of 0.3 to 0.5. The area ratio is an example of an "image feature value" according to the disclosed technology. The cell nucleus 61 and the cellular cytoplasm 62 are examples of a "structure of a cell" according to the disclosed technology. 0.3 to 0.5 is an example of a "threshold value" according to the disclosed technology. The area of the cell nucleus 61 is the total number of pixels discriminated as the cell nucleus 61 by the semantic segmentation. Similarly, the area of the cellular cytoplasm 62 is also the total number of pixels discriminated as the cellular cytoplasm 62 by the semantic segmentation.

This evaluation condition 44 relies on a statistical fact that the area ratio of the cell nucleus 61 to the cellular cytoplasm 62 is in a range of approximately 0.3 to 0.5. In a case where the average of the area ratios deviates from the range of 0.3 to 0.5, the evaluation condition relies on a consideration that there is a high probability that the trained model 41 erroneously discriminates the class of the semantic segmentation as illustrated in FIG. 6.

Figure 9:
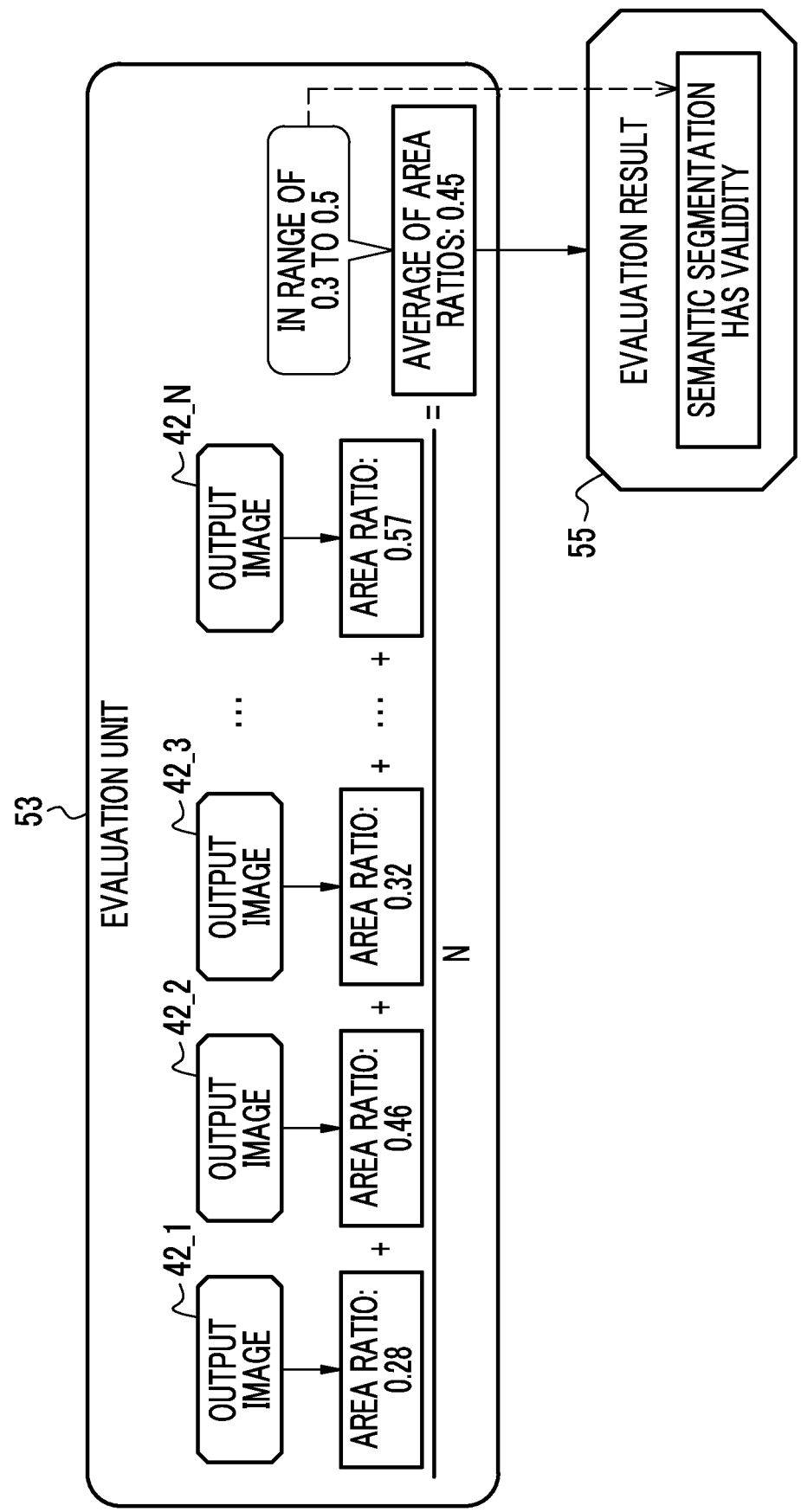
FIG. 9 is a diagram illustrating processing of the evaluation unit.
Figure 10:
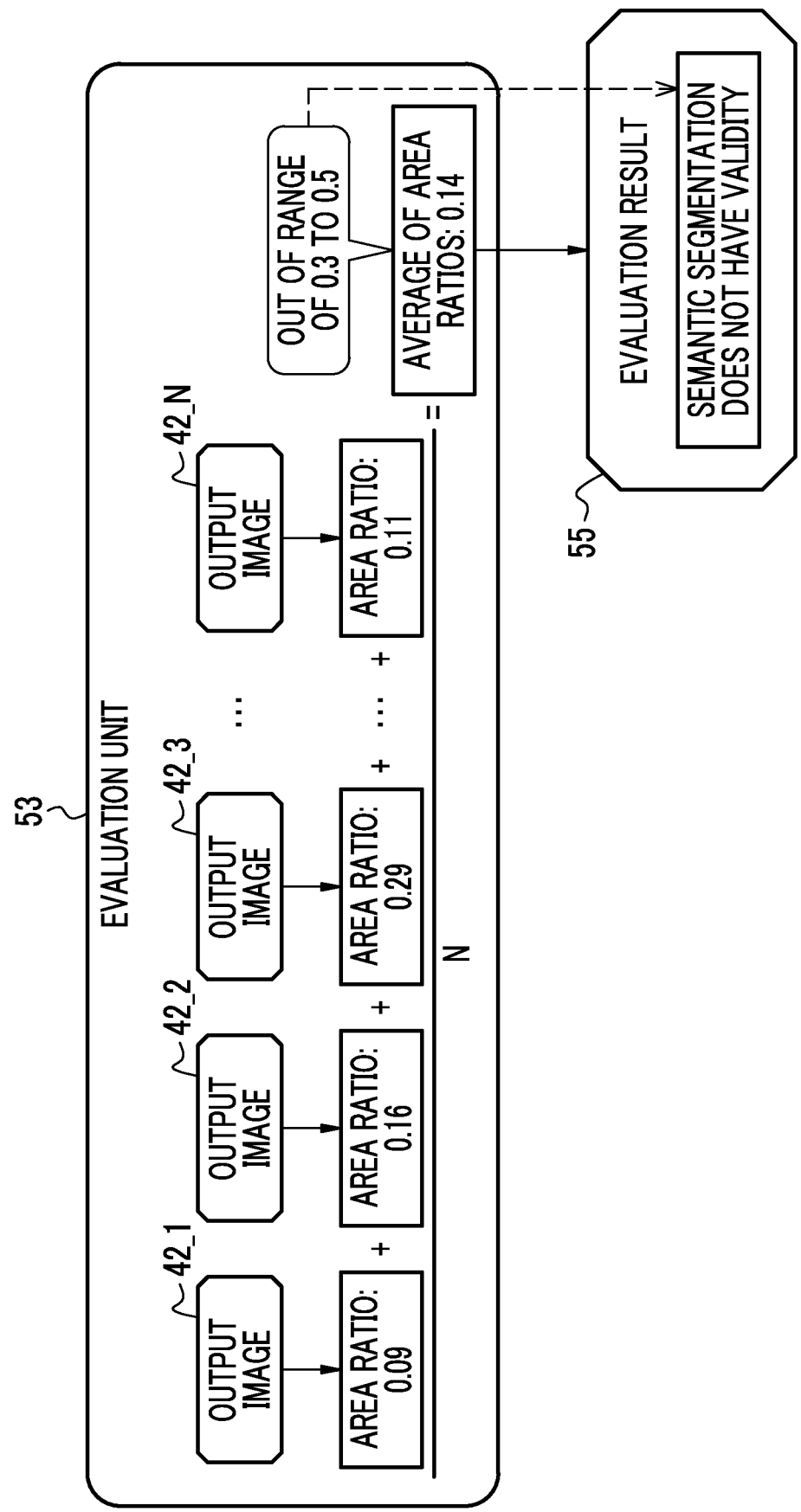
FIG. 10 is a diagram illustrating processing of the evaluation unit.

As illustrated in FIGS. 9 and 10, the evaluation unit 53 calculates the area ratio of the cell nucleus 61 to the cellular cytoplasm 62 for each of the output images 42_1 to 42_N. The average of the area ratios is calculated by dividing the sum of the calculated area ratios by N.

The evaluation unit 53 compares the calculated average of the area ratios with the range of 0.3 to 0.5 which is the average of the area ratios in the evaluation condition 44. As illustrated in FIG. 9, in a case where the calculated average of the area ratios is within the range of the average of the area ratios in the evaluation condition 44, the evaluation unit 53 evaluates that the semantic segmentation by the trained model 41 has validity. The evaluation unit 53 outputs the evaluation result 55 indicating that the semantic segmentation has validity. On the other hand, as illustrated in FIG. 10, in a case where the calculated average of the area ratios is out of the range of the average of the area ratios in the evaluation condition 44, the evaluation unit 53 evaluates that the semantic segmentation by the trained model 41 does not have validity. The evaluation unit 53 outputs the evaluation result 55 indicating that the semantic segmentation does not have validity.

Figure 11:
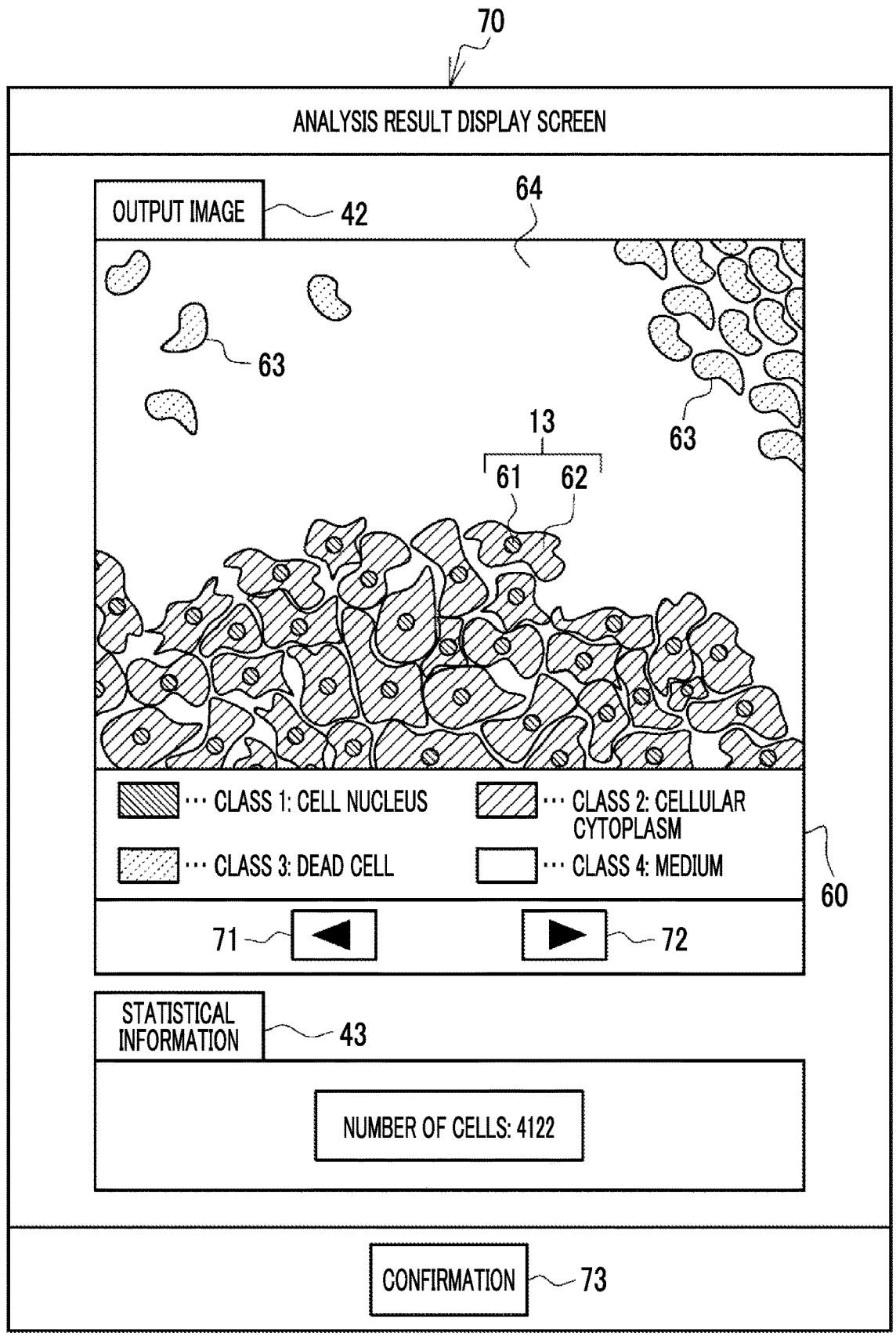
FIG. 11 is a diagram illustrating an analysis result display screen.
Figure 12:
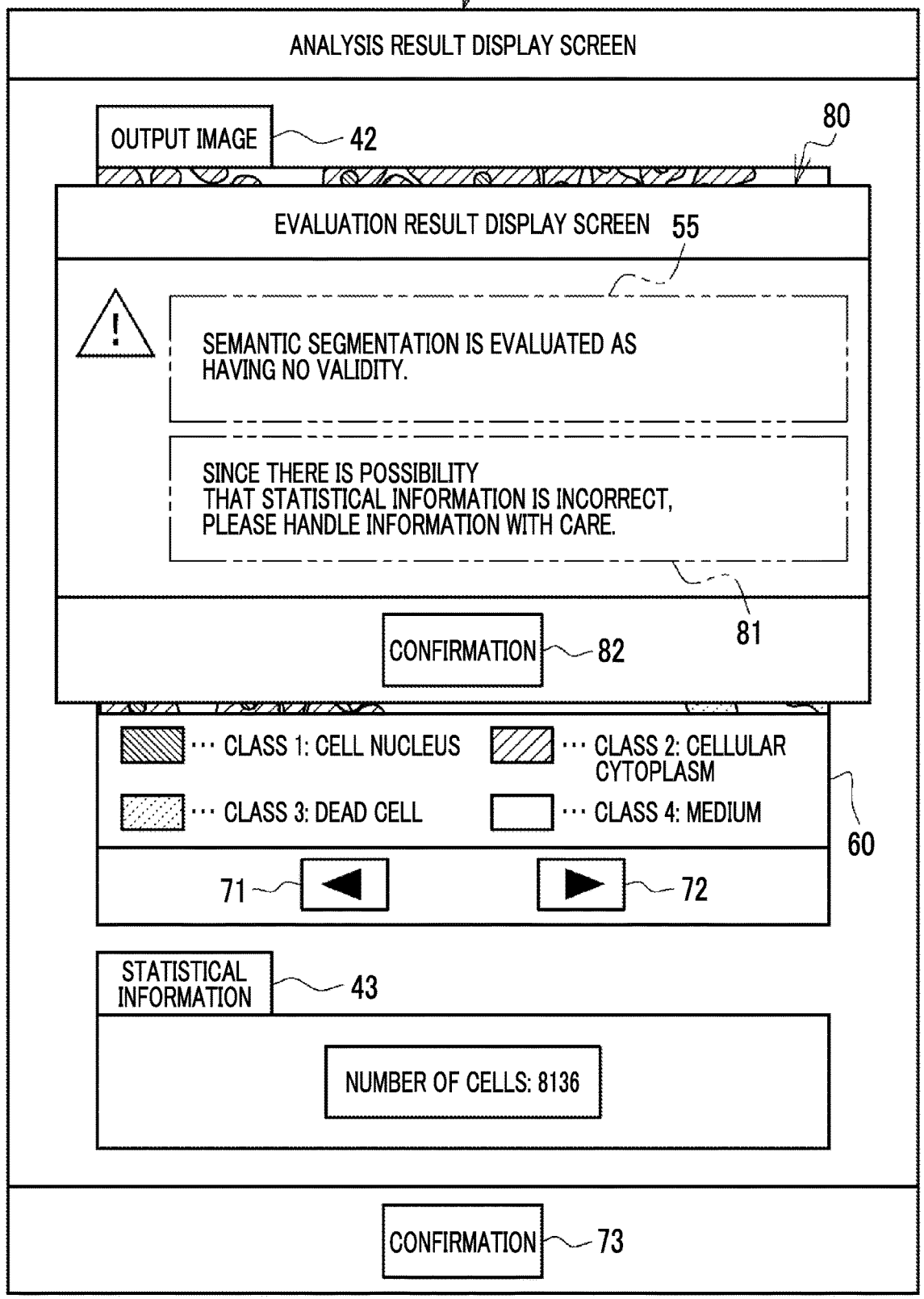
FIG. 12 is a diagram illustrating a state in which an evaluation result display screen is superimposed and displayed on the analysis result display screen.

As illustrated in FIGS. 11 and 12, the display controller 54 performs control such that the analysis result display screen 70 is displayed on the display 34. The output image 42 and the statistical information 43 are displayed on the analysis result display screen 70. The explanatory note 60 of the class is displayed at a lower part of the output image 42. A rewind button 71 and a forward button 72 are provided at a lower part of the explanatory note 60. The rewind button 71 is selected in a case where one output image 42 to be displayed from among the plurality of output images 42_1 to 42_N is shifted backward. The forward button 72 is selected in a case where one output image 42 to be displayed from among the plurality of output images 42_1 to 42_N is shifted forward. The display of the analysis result display screen 70 disappears in a case where a confirmation button 73 is selected.

FIG. 11 shows a case where the evaluation result 55 indicating that the semantic segmentation by the trained model 41 has validity is output from the evaluation unit 53. On the other hand, FIG. 12 shows a case where the evaluation result 55 indicating that the semantic segmentation by the trained model 41 does not have validity is output from the evaluation unit 53. In this case, the display controller 54 superimposes and displays the evaluation result display screen 80 on the analysis result display screen 70.

The evaluation result 55 indicating that the semantic segmentation by the trained model 41 does not have validity is displayed on the evaluation result display screen 80. A warning 81 indicating that the reliability of the statistical information 43 is low is displayed on the evaluation result display screen 80. The display of the evaluation result display screen 80 disappears in a case where the confirmation button 82 is selected.

Next, actions of the above configuration will be described with reference to the flowcharts of FIGS. 13 and 14. First, in a case where the operating program 40 is activated in the information processing apparatus 10, as illustrated in FIG. 4, the CPU 32 of the information processing apparatus 10 functions as the RW controller 50, the processing unit 51, the derivation unit 52, the evaluation unit 53, and the display controller 54.

Figure 13:
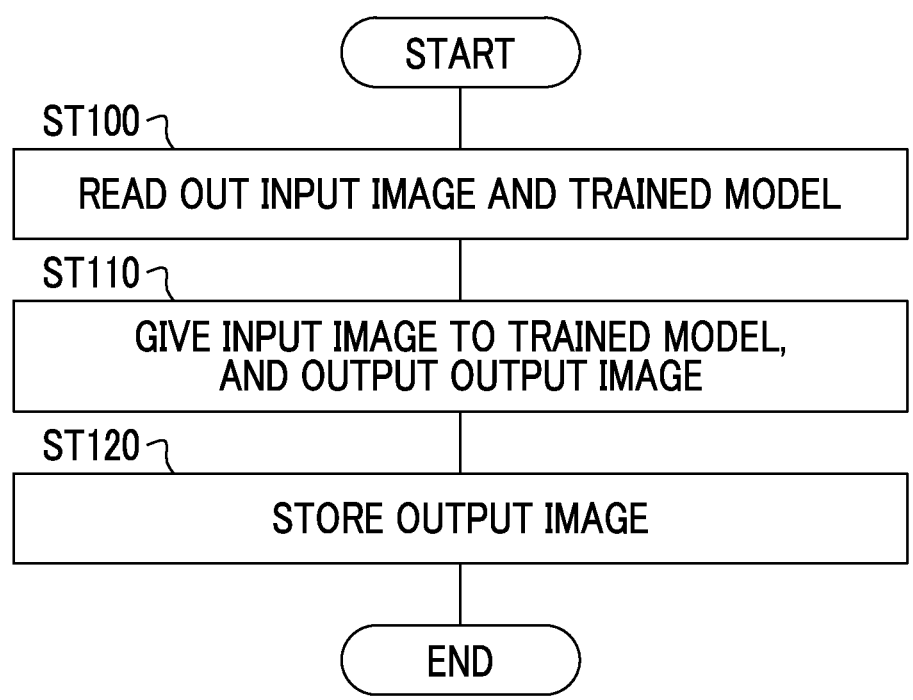
FIG. 13 is a flowchart illustrating a processing procedure of the information processing apparatus.

As illustrated in FIG. 13, the input image 12 and the trained model 41 are read out from the storage device 30 by the RW controller 50 (step ST100). The input image 12 and the trained model 41 are output from the RW controller 50 to the processing unit 51.

In the processing unit 51, the input image 12 is given to the trained model 41. The output image 42 for which the class of the object appearing in the input image 12 is discriminated is output from the trained model 41 (step ST110). The output image 42 is output from the processing unit 51 to the RW controller 50, and is stored in the storage device 30 by the RW controller 50 (step ST120). These steps ST100 to ST120 are performed for the plurality of input images 12 for the plurality of regions 20. Thus, the storage device 30 finally stores the output images 42_1 to 42_N.

Figure 14:
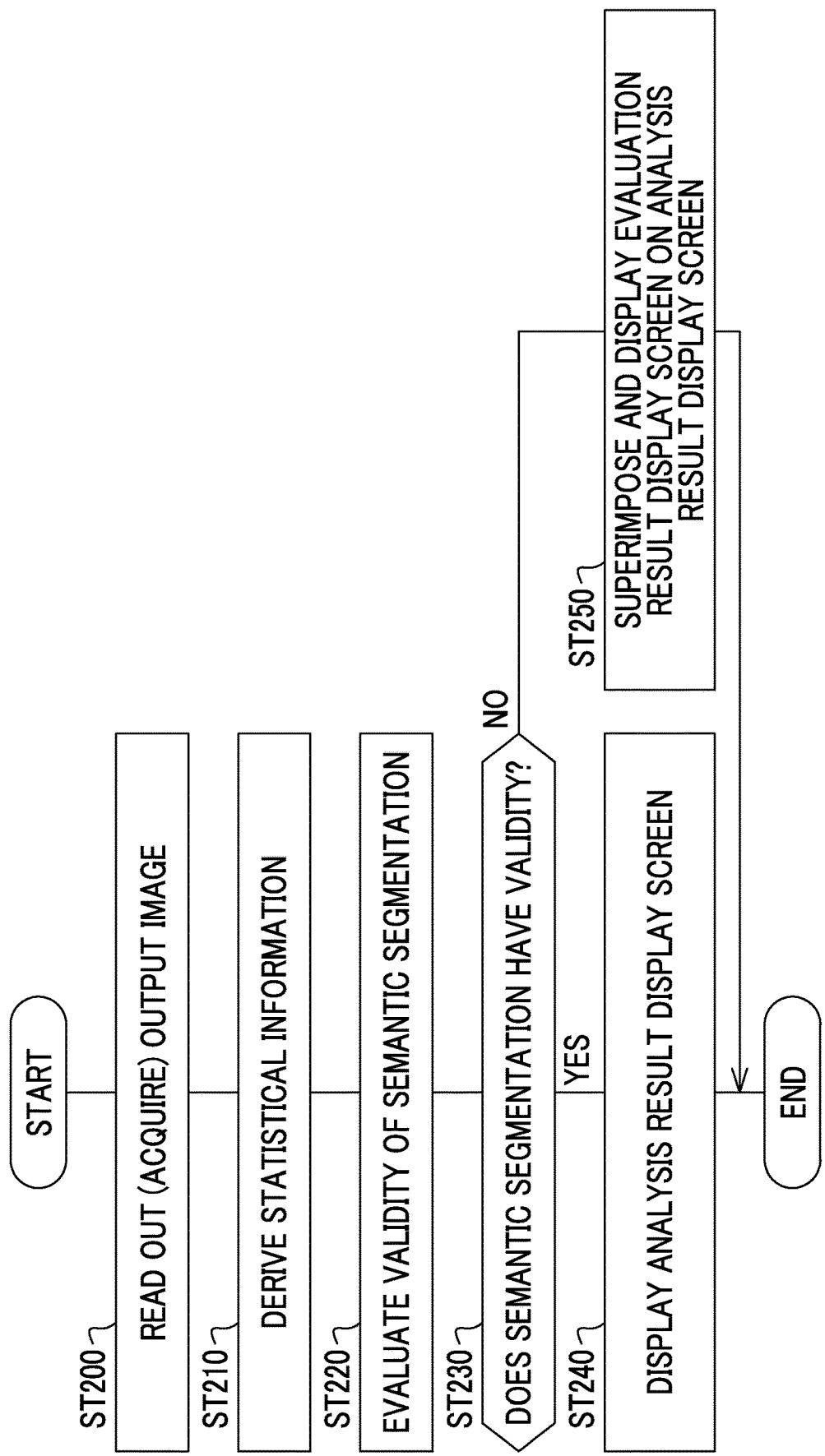
FIG. 14 is a flowchart illustrating a processing procedure of the information processing apparatus.

As illustrated in FIG. 14, the output images 42 (output images 42_1 to 42_N) are read out from the storage device 30 the RW controller 50 (step ST200). The output image 42 is output from the RW controller 50 to the derivation unit 52 and the evaluation unit 53. Step ST200 is an example of an "acquisition step" according to the disclosed technology.

As illustrated in FIG. 7, the statistical information 43 is derived by the derivation unit 52 based on the output image 42 (step ST210). The statistical information 43 is output from the derivation unit 52 to the RW controller 50, and is stored in the storage device 30 by the RW controller 50.

As illustrated in FIGS. 9 and 10, the evaluation unit 53 evaluates the validity of the semantic segmentation by the trained model 41 based on the output image 42 and the evaluation condition 44 (step ST220). The evaluation result 55 of the validity of the semantic segmentation by the trained model 41 is output from the evaluation unit 53 to the display controller 54. Step ST220 is an example of an "evaluation step" according to the disclosed technology.

In a case where the evaluation result 55 indicating that the semantic segmentation by the trained model 41 has validity is output from the evaluation unit 53 (YES in step ST230), the analysis result display screen 70 is obtained on the display 34 by the display controller 54 as illustrated in FIG. 11 (step ST240).

On the other hand, in a case where the evaluation result 55 indicating that the semantic segmentation by the trained model 41 does not have validity is output from the evaluation unit 53 (NO in step ST230), the evaluation result display screen 80 is superimposed and displayed on the analysis result display screen 70 the display controller 54 as illustrated in FIG. 12 (step ST250). Step ST250 is an example of a "display control step" according to the disclosed technology.

As described above, the information processing apparatus 10 includes the RW controller 50 as the acquisition unit, the evaluation unit 53, and the display controller 54. The RW controller 50 acquires the output image 42 by reading out the output image 42 output from the trained model 41 from the storage device 30. The evaluation unit 53 evaluates the validity of the semantic segmentation by the trained model 41 based on the output image 42. In a case where the evaluation unit 53 evaluates that the semantic segmentation by the trained model 41 does not have validity, the display controller 54 performs control such that the evaluation result display screen 80 including the evaluation result 55 indicating that the semantic segmentation by the trained model 41 does not have validity is displayed on the display 34. Accordingly, it is possible to reliably notify that the semantic segmentation by the trained model 41 does not have validity.

The evaluation unit 53 calculates, as the image feature value, the area ratio obtained by dividing the area of the cell nucleus 61 by the area of the cellular cytoplasm 62 from the output image 42. The validity of the semantic segmentation by the trained model 41 is evaluated by using the area ratio. Accordingly, the reliability of the evaluation result 55 can be improved as compared with a case where a feature value other than the image feature value of the output image 42 is used for evaluation. Since the area ratio can be easily calculated, the validity can be easily evaluated.

The information processing apparatus 10 includes the derivation unit 52 for deriving the statistical information 43 of the object appearing in the input image 12 based on the output image 42. In a case where the evaluation unit 53 evaluates that the semantic segmentation by the trained model 41 does not have validity, the display controller 54 performs control such that the warning 81 indicating that the reliability of the statistical information 43 is low is displayed together with the evaluation result 55. Accordingly, in addition to the fact that the semantic segmentation by the trained model 41 does not have validity, it is also possible to notify that the reliability of the statistical information 43 is low. It is possible to effectively prevent the statistical information 43 having low reliability from being erroneously referred to.

Here, the field of the cell culture has recently been spotlighted with the advent of induced pluripotent stem (iPS) cells and the like. Thus, there is a demand for a technology that can surely notify that the discrimination of the class of the object within the cell image by the trained model 41 does not have validity. In the disclosed technology, the cell image obtained by imaging the plurality of cells 13 in culture is used as the input image 12. Accordingly, it can be said that the disclosed technology is a technology that can meet recent demands.

Second Embodiment

It is considered that the area ratio obtained by dividing the area of the cell nucleus 61 by the area of the cellular cytoplasm 62 differs depending on the type of the cell 13. Similarly, it is considered that the area ratio differs depending on the number of culture days of the cell 13. Thus, in the second embodiment illustrated in FIGS. 15 to 17, the threshold value used for evaluating the validity of the semantic segmentation by the trained model 41 in comparison with the area ratio changes according to the type of the cell 13 and/or the number of culture days of the cell 13.

Table 85 illustrated in FIG. 15 is an example in which the threshold value changes according to the type of the cell 13. Examples of the type of the cell 13 include a nerve cell, a myocardial cell, a hepatocyte, and the like. An example of the threshold value is 0.3 to 0.5 for the nerve cell, is 0.2 to 0.5 for the myocardial cell, and is 0.4 to 0.6 for the hepatocyte. In this case, it is premised that the trained model 41 is a model using a plurality of types of cells 13 as targets.

Table 86 illustrated in FIG. 16 is an example in which the threshold value changes according to the number of culture days of the cell 13. The threshold value is 0.1 to 0.3 in a case where the number of culture days of the cell 13 is on the first day, is 0.2 to 0.4 in a case where the number of culture days of the cell is on the second day, and is 0.3 to 0.5 in a case where the number of culture days of the cell is on the third day.

Table 87 illustrated in FIG. 17 is an example in which the threshold value changes according to the type and the number of culture days of the cell 13. Examples of the type of the cell include a nerve cell, a myocardial cell, a hepatocyte, and the like, as in Table 85 illustrated in FIG. 15. For example, the example of the threshold value of the nerve cell is 0.2 to 0.3 in a case where the number of culture days is on the first day, is 0.22 to 0.33 in a case where the culture days are on the second day, and is 0.24 to 0.38 in a case where the culture days are on the third day.

As described above, in the second embodiment, the threshold value used for evaluating the validity of the semantic segmentation by the trained model 41 as compared with the area ratio changes according to the type of the cell 13 and/or the number of culture days of the cell 13. Accordingly, it is possible to evaluate the validity of the semantic segmentation by the trained model 41 adapted to the type of the cell 13 and/or the number of culture days of the cell 13.

Third Embodiment

As described in FIG. 6, in the trained model 41, the periodic noise caused by dividing the well 14 into the plurality of regions 20 and imaging the divided regions may be erroneously discriminated as the cell nucleus 61 of class 1 or the cellular cytoplasm 62 of class 2. Thus, in the third embodiment illustrated in FIGS. 18 to 21, an entire image 98 representing the entire well 14 is generated, and the intensity of the periodic noise of the entire image 98 is calculated as the image feature value.

Figure 18:
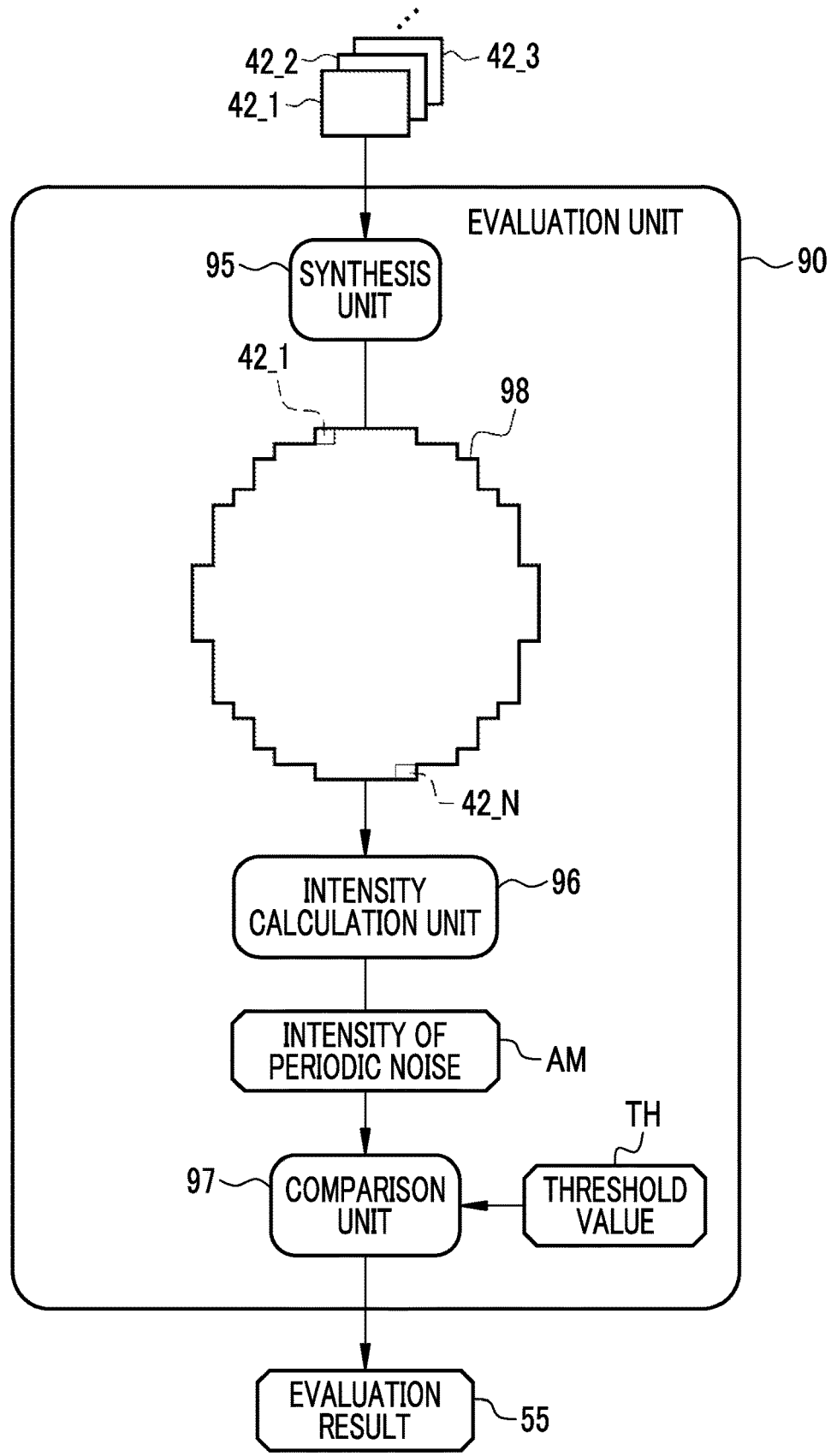
FIG. 18 is a diagram illustrating an evaluation unit according to a third embodiment.

In FIG. 18, an evaluation unit 90 of the third embodiment includes a synthesis unit 95, an intensity calculation unit 96, and a comparison unit 97. The synthesis unit 95 generates the entire image 98 representing the entire well 14 by joining the plurality of output images 42_1 to 42_N corresponding to the input images 12 for the plurality of regions 20 obtained by dividing the well 14. The processing of generating the entire image 98 by joining the fragmentary output images 42_1 to 42_N in this manner is also called tiling. The synthesis unit 95 outputs the entire image 98 to the intensity calculation unit 96.

The intensity calculation unit 96 performs a Fourier transform on the entire image 98 to generate a Fourier spectrum 102 (see FIGS. 20 and 21) of the entire image 98. The intensity calculation unit 96 calculates an intensity AM of a periodic noise of the entire image 98 which is caused by dividing the well 14 into the plurality of regions 20 and imaging the divided regions from the generated Fourier spectrum 102. A frequency F of the periodic noise (see FIGS. 20 and 21) can be obtained in advance from the size, the number, and the like of the region 20. The intensity calculation unit 96 calculates, as the intensity AM of the periodic noise, the intensity of the Fourier spectrum 102 of the obtained frequency F. The intensity calculation unit 96 outputs the intensity AM of the periodic noise to the comparison unit 97.

The comparison unit 97 compares the magnitude of the intensity AM of the periodic noise with a preset threshold value TH. The evaluation result 55 corresponding to this comparison result is output.

Figure 19:
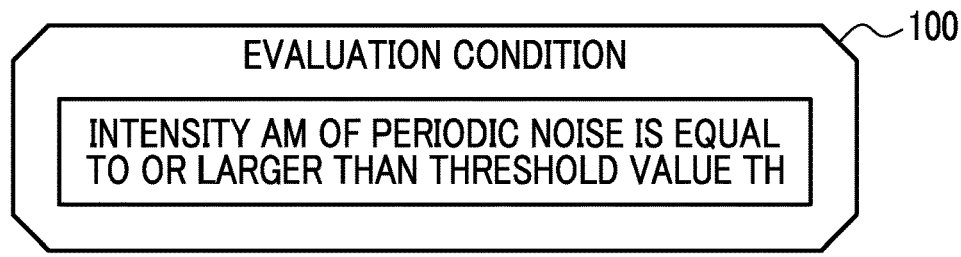
FIG. 19 is a diagram illustrating an evaluation condition according to the third embodiment.

As illustrated in FIG. 19, an evaluation condition 100 of the third embodiment is a content indicating that the semantic segmentation by the trained model 41 is evaluated as having no validity in a case where the intensity AM of the periodic noise is equal to or larger than the threshold value TH.

Figure 20:
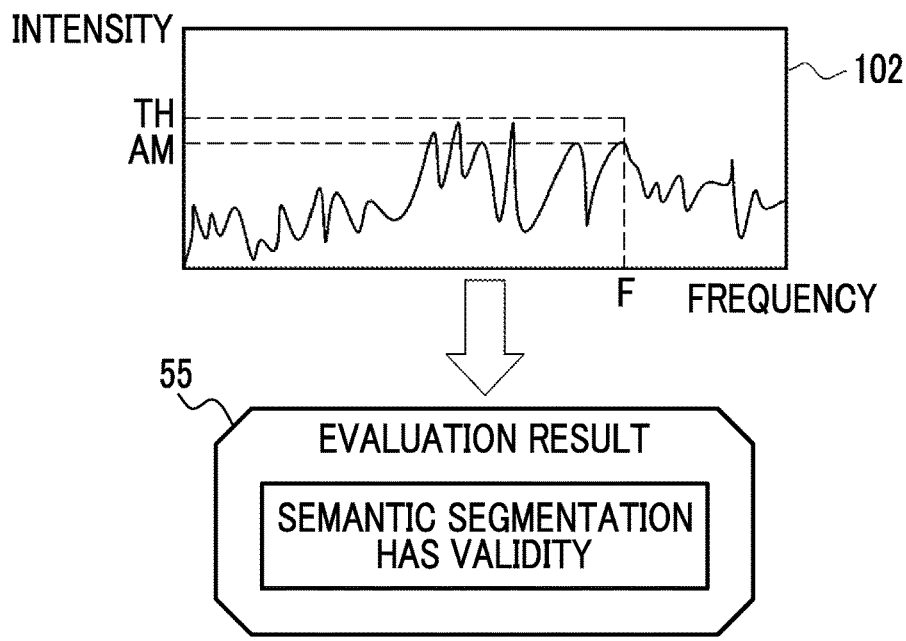
FIG. 20 is a diagram illustrating processing of the evaluation unit according to the third embodiment.
Figure 21:
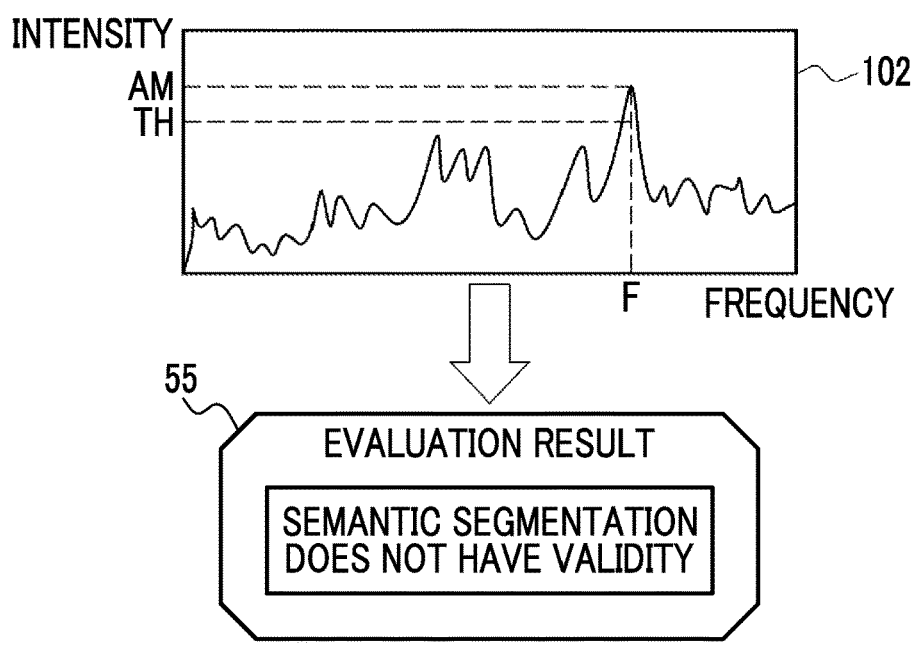
FIG. 21 is a diagram illustrating processing of an evaluation unit according to a third embodiment.

As illustrated in FIG. 20, in a case where the intensity AM of the periodic noise is less than the threshold value TH, the evaluation unit 90 evaluates that the semantic segmentation by the trained model 41 has validity. The evaluation unit 90 outputs the evaluation result 55 indicating that the semantic segmentation has validity. On the other hand, as illustrated in FIG. 21, in a case where the intensity AM of the periodic noise is equal to or larger than the threshold value TH, the evaluation unit 90 evaluates that the semantic segmentation by the trained model 41 does not have validity. The evaluation unit 90 outputs the evaluation result 55 indicating that the semantic segmentation does not have validity.

As described above, in the third embodiment, the synthesis unit 95 generates the entire image 98 by joining the plurality of output images 42_1 to 42_N. The intensity calculation unit 96 calculates the intensity AM of the periodic noise of the entire image 98 as the image feature value. Accordingly, in a case where the trained model 41 erroneously discriminates the periodic noise from the cell nucleus 61 of class 1 or the cellular cytoplasm 62 of class 2, it is possible to evaluate that the semantic segmentation does not have validity.

The first and second embodiments in which the area ratio is calculated as the image feature value may be combined with the third embodiment. In this case, in a case where the average of the area ratios is out of the range of the average of the area ratios in the evaluation condition 44 and/or in a case where the intensity AM of the periodic noise is equal to or larger than the threshold value TH, the evaluation unit evaluates that the semantic segmentation by the trained model 41 does not have validity.

Fourth Embodiment

Figure 22:
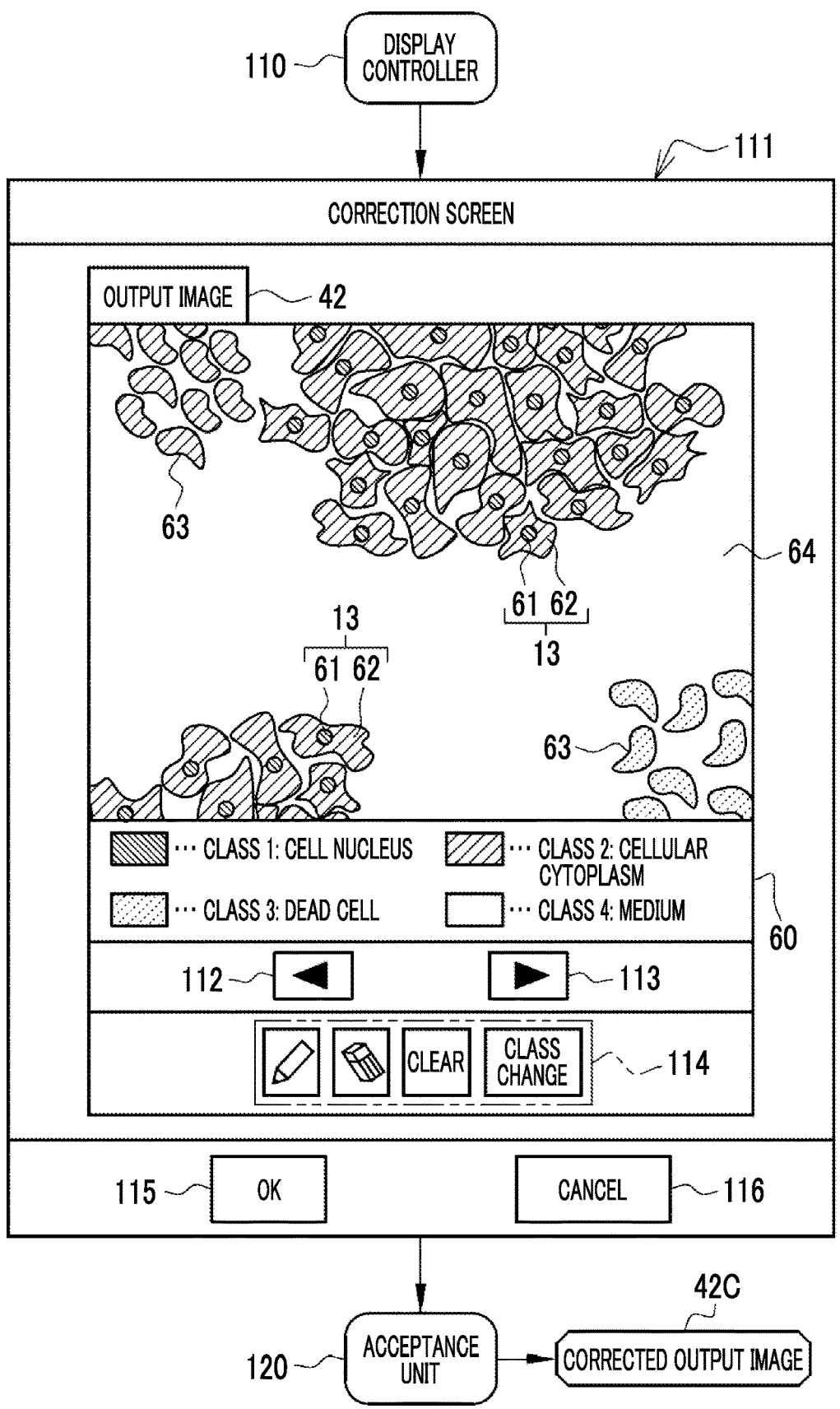
FIG. 22 is a diagram illustrating a correction screen.

In a fourth embodiment illustrated in FIG. 22, control is performed such that the output image 42 evaluated as having no validity of the semantic segmentation by the trained model 41 is displayed. A correction instruction for the class of the output image 42 evaluated as having no validity of the semantic segmentation by the trained model 41 is accepted.

In FIG. 22, a display controller 110 according to the fourth embodiment performs control such that a correction screen 111 is displayed on the display 34. For example, the display controller 110 turns off the display of the analysis result display screen 70, and then displays the correction screen 111 in place of the analysis result display screen 70. The output image 42 evaluated as having no validity of the semantic segmentation by the trained model 41 is displayed on the correction screen 111. That is, the display controller 110 is an example of an "output controller" according to the disclosed technology. FIG. 22 shows an example in which the output image 42 for which the dead cell 63 to be discriminated as class 3 is erroneously discriminated as the cellular cytoplasm 62 of class 2 illustrated in FIG. 6 is displayed.

Similarly to the rewind button 71 and the forward button 72 of the analysis result display screen 70, a rewind button 112 and a forward button 113 at the lower part of the explanatory note 60 of the class are selected in a case where one output image 42 to be displayed is shifted backward and in a case where on output image to be displayed is shifted forward, respectively. A correction button group 114 is provided at a lower part of the rewind button 112 and the forward button 113. Various buttons for correcting the class erroneously discriminated by the trained model 41 to the original class are provided in the correction button group 114.

A user corrects the class erroneously discriminated by the trained model 41 to the original class by operating the various buttons of the correction button group 114, and then selects an OK button 115. In a case where the OK button 115 is selected, an acceptance unit 120 accepts the correction instruction for the class of the output image 42. A corrected output image 42C of which the class is corrected according to this correction instruction is stored in the storage device 30 by the RW controller 50. In a case where a cancel button 116 is selected, the display of the correction screen 111 disappears.

As described above, in the fourth embodiment, the output image 42 evaluated as having no validity of the semantic segmentation by the trained model 41 is controlled to be displayed. The acceptance unit 120 accepts the correction instruction for the class of the output image 42 evaluated as having no validity of the semantic segmentation by the trained model 41. Accordingly, the corrected output image 42C of which the class is corrected can be used as learning data for re-training the trained model 41 together with the original input image 12. The discrimination accuracy of the class of the trained model 41 can be further improved by re-training the trained model 41 with the corrected output image 42C. As a result, it is possible to reduce a probability that the semantic segmentation by the trained model 41 is evaluated as having no validity.

A timing at which the correction screen 111 is displayed on the display 34 is not limited to after the display of the analysis result display screen 70 is turned off. The output image 42 evaluated as having no validity of the semantic segmentation by the trained model 41 may be stored in the storage device 30, and the correction screen 111 may be displayed on the display 34 according to the request of the user.

A form in which the output image 42 evaluated as having no validity of the semantic segmentation by the trained model 41 is output is not limited to a form in which the output image 42 evaluated as having no validity of the semantic segmentation by the trained model 41 is displayed as described above. A form in which the output image 42 evaluated as having no validity of the semantic segmentation by the trained model 41 is output to the RW controller 50 in order to store the output image in the storage device 30 may be used. Alternatively, a form in which the output image 42 evaluated as having no validity of the semantic segmentation by the trained model 41 is transmitted to another apparatus connected to the information processing apparatus 10 via a network may be used.

An apparatus that receives the output images 42 evaluated as having no validity of the semantic segmentation by the trained model 41 from a plurality of information processing apparatuses 10 via a network and collectively manage the output images 42 may be provided.

Fifth Embodiment

Figure 23:
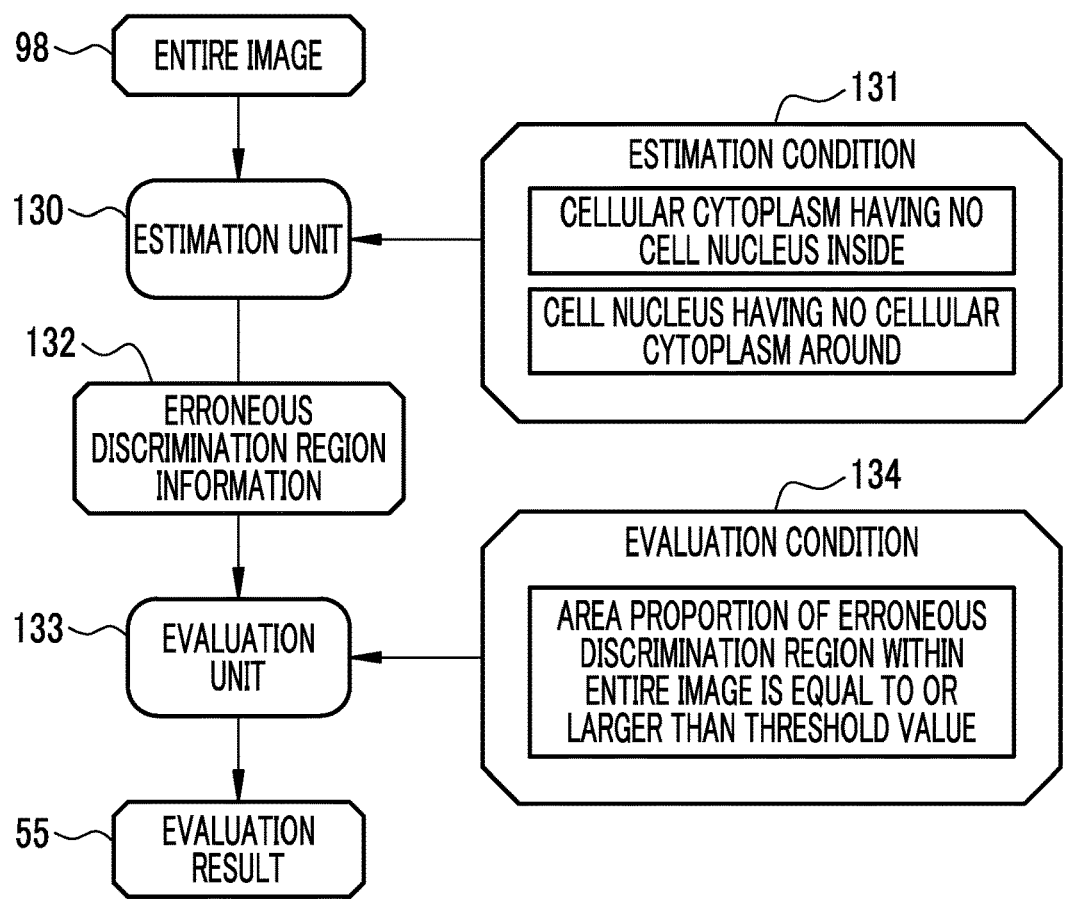
FIG. 23 is a diagram illustrating an aspect in which an erroneous discrimination region in which a class is erroneously discriminated is estimated from an entire image and evaluation is performed based on erroneous discrimination region information.
Figure 24:
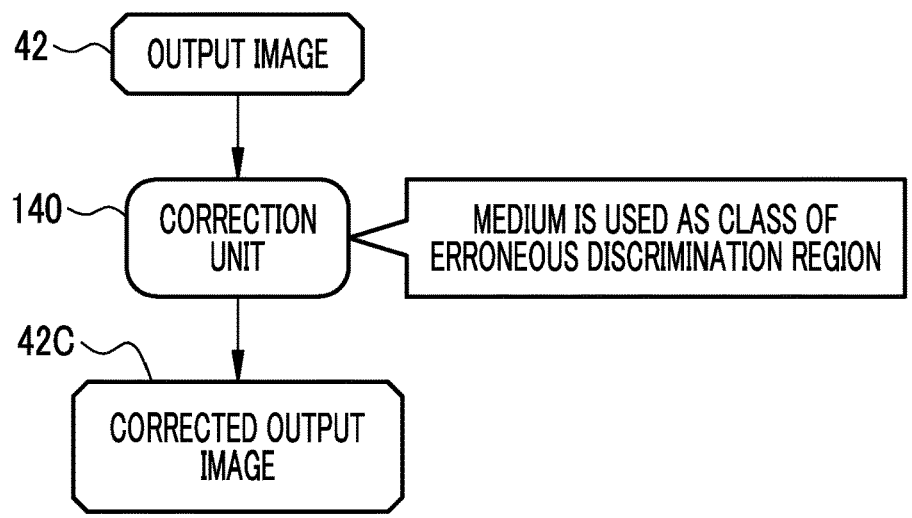
FIG. 24 is a diagram illustrating an aspect in which the class of the output image evaluated as having no validity of semantic segmentation by a trained model is corrected.

In a fifth embodiment illustrated in FIGS. 23 and 24, an erroneous discrimination region in which the class is erroneously discriminated is estimated from the entire image 98. The output image 42 is corrected by correcting the class of the erroneous discrimination region.

In FIG. 23, the entire image 98 is input to an estimation unit 130. The estimation unit 130 estimates the erroneous discrimination region in which the class is erroneously discriminated from the entire image 98 according to an estimation condition 131. The estimation condition 131 is a content indicating that the cellular cytoplasm 62 having no cell nucleus 61 inside and the cell nucleus 61 having no cellular cytoplasm 62 around are set as the erroneous discrimination regions. An estimation unit 130 outputs erroneous discrimination region information 132 which is an estimation result of the erroneous discrimination region to the evaluation unit 133. The erroneous discrimination region information 132 is information on coordinates of the erroneous discrimination region in the entire image 98.

The evaluation unit 133 according to the fifth embodiment calculates, as the image feature value, an area proportion of the erroneous discrimination region within the entire image 98 based on the erroneous discrimination region information 132. An evaluation condition 134 in this case is a content indicating that the semantic segmentation by the trained model 41 is evaluated as having no validity in a case where the area proportion of the erroneous discrimination region within the entire image 98 is equal to or larger than a preset threshold value. In a case where the area proportion of the erroneous discrimination region within the entire image 98 is less than the threshold value, the evaluation unit 133 outputs the evaluation result 55 indicating that the semantic segmentation has validity. On the other hand, in a case where the area proportion of the erroneous discrimination region within the entire image 98 is equal to or larger than the threshold value, the evaluation unit 133 outputs the evaluation result 55 indicating that the semantic segmentation does not have validity.

In FIG. 24, a correction unit 140 corrects the output image 42 evaluated as having no validity of the semantic segmentation by the trained model 41 to obtain the corrected output image 42C. Specifically, the correction unit 140 sets a class of the erroneous discrimination region within the output image 42 to the uniform medium 64. The corrected output image 42C is stored in the storage device 30 by the RW controller 50.

As described above, in the fifth embodiment, the correction unit 140 corrects the class of the output image 42 evaluated as having no validity of the semantic segmentation by the trained model 41. Accordingly, it is possible to reduce a burden on the user as compared with a case where the correction of the class is entirely entrusted to the user as in the fourth embodiment. As in the fourth embodiment, the corrected output image 42C can be used as the learning data for re-training the trained model 41, and the discrimination accuracy of the class of the trained model 41 can be further improved.

After the class is automatically corrected by the correction unit 140, the user may accept the correction instruction for the class. Since the user only needs to correct the class that cannot be completely corrected by the correction unit 140, the effect that the burden on the user can be reduced can be exhibited in this case as well.

Sixth Embodiment

Figure 25:
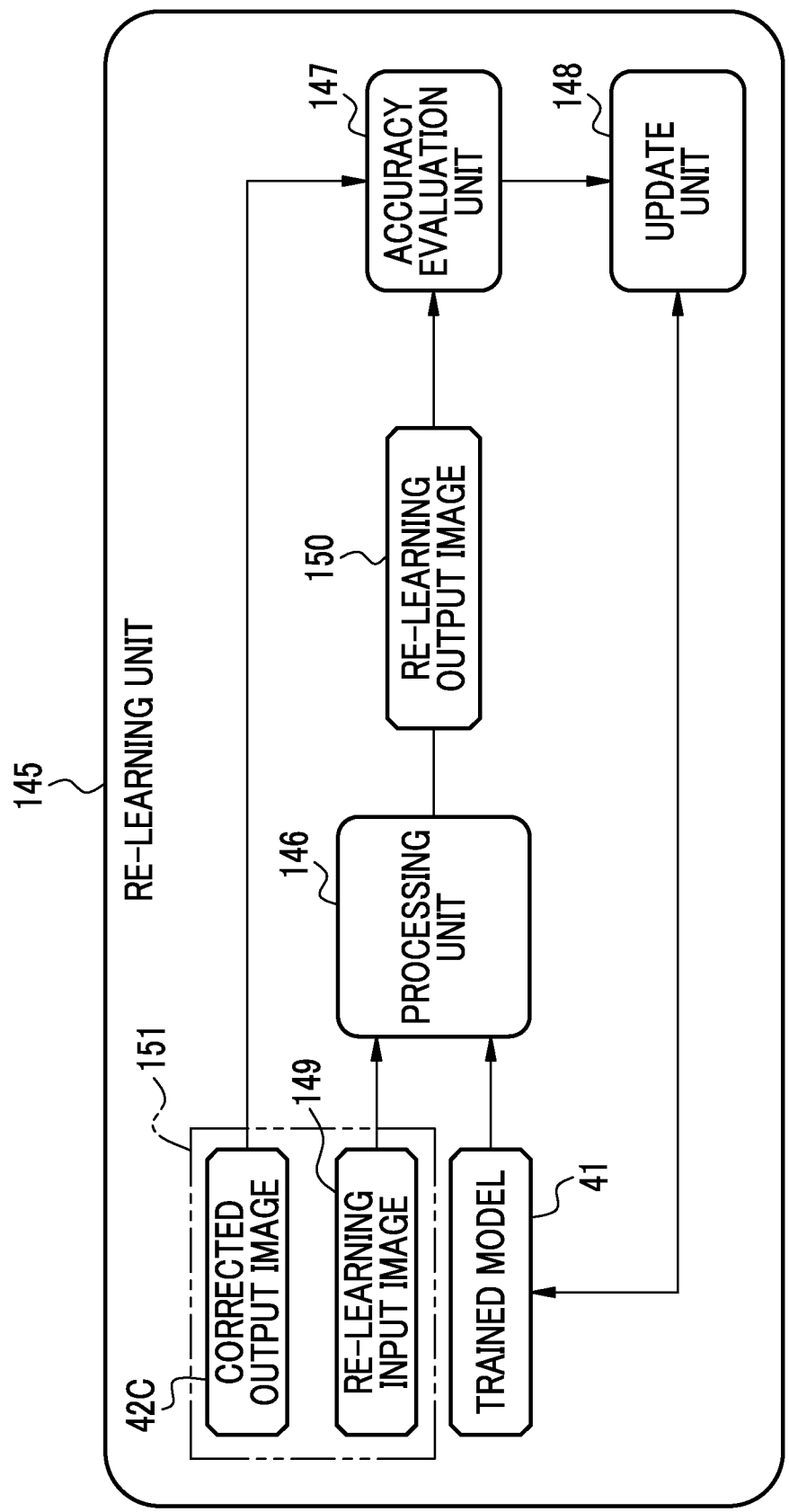
FIG. 25 is a block diagram illustrating a re-learning unit.

In a sixth embodiment illustrated in FIG. 25, the corrected output image 42C according to the fourth embodiment and the fifth embodiment is used as the learning data, and the trained model 41 is re-trained.

In FIG. 25, a re-learning unit 145 has a processing unit 146, an accuracy evaluation unit 147, and an update unit 148. The processing unit 146 gives a re-learning input image 149 to the trained model 41, and outputs a re-learning output image 150 from the trained model 41. The processing unit 146 outputs the re-learning output image 150 to the accuracy evaluation unit.

The re-learning input image 149 is the input image 12 input to the trained model 41 by the processing unit 51 in a case where the original output image 42 of the corrected output image 42C is output from the trained model 41. Learning data 151 includes the re-learning input image 149 and the corrected output image 42C.

The accuracy evaluation unit 147 compares the corrected output image 42C with the re-learning output image 150, and evaluates the discrimination accuracy of the class of the trained model 41. The accuracy evaluation unit 147 evaluates the discrimination accuracy of the class of the trained model 41 by using a loss function. The loss function is a function representing a degree of difference in designation of the class between the corrected output image 42C and the re-learning output image 150. As a calculated value of the loss function becomes closer to zero, the discrimination accuracy of the class of the trained model 41 becomes higher. The accuracy evaluation unit 147 outputs an evaluation result of the discrimination accuracy of the class of the trained model 41 by the loss function to the update unit 148.

The update unit 148 updates the trained model 41 according to the evaluation result from the accuracy evaluation unit 147. For example, the update unit 148 changes values of various parameters of the trained model 41 by a stochastic gradient descent method or the like accompanied by a learning coefficient. The learning coefficient indicates a range of change in the values of the parameters. That is, as the learning coefficient is a relatively larger value, the range of change in the values of the parameters becomes wider, and a degree of update of the trained model 41 becomes larger.

The re-learning unit 145 repeats the input of the re-learning input image 149 to the trained model 41 by the processing unit 146, the output of the re-learning output image 150 to the accuracy evaluation unit 147, the evaluation of the discrimination accuracy of the class of the trained model 41 by the accuracy evaluation unit 147, and the update of the trained model 41 by the update unit 148 until the discrimination accuracy of the class of the trained model 41 reaches a preset level. The re-learning unit 145 outputs the trained model 41 of which the discrimination accuracy of the class reaches the preset level to the RW controller 50. The RW controller 50 stores the trained model 41 from the re-learning unit 145 in the storage device 30, reads out the trained model, and outputs the trained model to the processing unit 51.

The re-learning unit 145 causes the trained model 41 to perform mini-batch learning using, for example, mini-batch data. The mini-batch data is a part (for example, 100 images) of a plurality of divided images obtained by dividing the corrected output image 42C and the re-learning input image 149 (for example, 10,000 divided images divided by frames each having a size of $\frac{1}{100}$ of the original image). The re-learning unit 145 trains the trained model 41 by creating a plurality of sets (for example, 100 sets) of mini-batch data and sequentially giving the sets to the trained model.

As described above, in the sixth embodiment, the corrected output image 42C obtained by correcting the class of the output image 42 evaluated as having no validity of the semantic segmentation by the re-learning unit 145 is used as the learning data 151, and the trained model 41 is re-trained. Accordingly, the discrimination accuracy of the class of the trained model 41 can be easily improved as compared with a case where the re-training of the trained model 41 is performed by another apparatus. The trained model 41 having improved discrimination accuracy of the class can be immediately given to the processing unit 51 and can be used.

Figure 26:
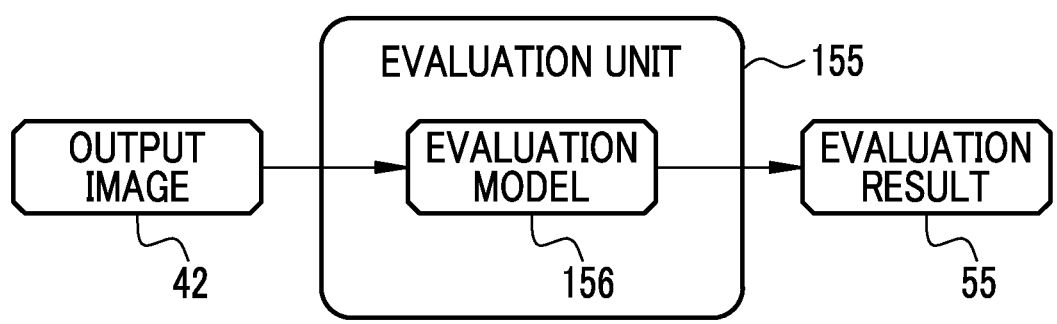
FIG. 26 is a diagram illustrating an aspect in which validity of the semantic segmentation by the trained model is evaluated by using an evaluation model.

In each of the above embodiments, although the validity of the semantic segmentation by the trained model 41 is evaluated by using the image feature value, the present invention is not limited thereto. As in the evaluation unit 155 illustrated in FIG. 26, the validity of the semantic segmentation by the trained model 41 may be evaluated by using an evaluation model 156. The evaluation model 156 is a machine learning model that outputs the evaluation result 55 in a case where the output image 42 is input. The evaluation model 156 is a model trained by giving a pair of the output image 42 and the evaluation result 55 as the learning data. By doing so, it is possible to omit the processing of calculating the image feature value.

The image feature value is not limited to the illustrated area ratio and intensity AM of the periodic noise. A parameter related to the shape of the cell 13, such as circularity of the cell 13, may be used as the image feature value. In a case where the parameter related to the shape of the cell 13 is used as the image feature value, the threshold value used for evaluating the validity of the semantic segmentation by the trained model 41 may change according to the type of the cell 13 and/or the number of culture days of the cell 13 by applying the second embodiment.

The statistical information 43 is not limited to the number of cells 13 illustrated above. A total area of the cell 13 in the entire image 98 may be used, or an area ratio of the area of the cell nucleus 61 divided by the area of the cellular cytoplasm 62 which is illustrated as the image feature value may be used.

In each of the above embodiments, although the cell image obtained by imaging the plurality of cells 13 in culture is illustrated as the input image 12 and the cell nucleus 61, the cellular cytoplasm 62, and the like are illustrated as the class, the present invention is not limited thereto. Nucleolus which is a type of the structure of the cell may be used as the class. Live cells, dead cells, differentiated cells, undifferentiated cells, and the like may be used as the class. In this case, for example, an area ratio obtained by dividing the area of the differentiated cell by the area of the undifferentiated cell is calculated as the image feature value. In a case where the plurality of cells 13 are cultured in one well 14, each of the plurality of cells 13 may be used as the class.

A satellite moving image obtained by imaging a road may be used as the input image 12, a car may be used as the class, and the number of cars may be derived as the statistical information 43. Alternatively, a moving image obtained by imaging a street may be used as the input image 12, a person may be used as the class, and the number of persons may be used as the statistical information 43.

A hardware configuration of the computer constituting the information processing apparatus 10 can be modified in various ways. It is also possible to constitute the information processing apparatus 10 by a plurality of computers separated as hardware in order to improve processing capability and reliability. For example, the function of the processing unit 51 of the information processing apparatus 10 and the functions of the derivation unit 52 and the evaluation unit 53 are distributed to two computers. In this case, the information processing apparatus 10 is constituted by two computers.

As described above, the hardware configuration of the computer of the information processing apparatus 10 can be appropriately changed according to required performance such as processing capability, safety, and reliability. Not only hardware but also an application program such as the operating program 40 or the like can be duplicated or can be distributed and stored in a plurality of storage devices in order to ensure safety and reliability.

In each of the above embodiments, for example, the following various processors can be used as a hardware structure of the processing units that execute various kinds of processing such as the RW controller 50, the processing units 51 and 146, the derivation unit 52, the evaluation units 53, 90, 133, and 155, the display controllers 54 and 110, the synthesis unit 95, the intensity calculation unit 96, the comparison unit 97, the acceptance unit 120, the estimation unit 130, the correction unit 140, the accuracy evaluation unit 147, and the update unit 148. As described above, in addition to the CPU 32 which is a general-purpose processor that functions as various processing units by executing software (operating program 40), the various processors include a programmable logic device (PLD), which is a processor capable of changing a circuit configuration after manufacture, such as a field programmable gate array (FPGA), and a dedicated electrical circuit, which is a processor having a circuit configuration specifically designed in order to execute specific processing such as an application specific integrated circuit (ASIC).

One processing unit may be constituted by one of these various processors, or may be constituted by a combination of two or more processors of the same type or different types (for example, a combination of a plurality of FPGAs and/or a combination of a CPU and a FPGA). The plurality of processing units may be constituted by one processor.

As an example in which the plurality of processing units are constituted by one processor, firstly, one processor is constituted by a combination of one or more CPUs and software as represented by computers such as clients and servers, and this processor functions as the plurality of processing units. Secondly, a processor that realizes the functions of the entire system including the plurality of processing units via one integrated circuit (IC) chip is used as represented by a system on chip (SoC). As described above, the various processing units are constituted by using one or more of the various processors as the hardware structure.

More specifically, an electric circuitry in which circuit elements such as semiconductor elements are combined can be used as the hardware structure of these various processors.

From the above description, the invention described in the following Appendix 1 can be grasped.

[Appendix 1]

An information processing apparatus includes an acquisition processor that acquires an output image output from a trained model as a result of causing the trained model to perform semantic segmentation in which discrimination of a class which is a type of an object appearing in an input image is performed on a pixel-by-pixel basis, an evaluation processor that evaluates validity of the semantic segmentation based on the output image, and a display control processor that performs control such that an evaluation result indicating that the semantic segmentation does not have validity is displayed in a case where the evaluation processor evaluates that the semantic segmentation does not have validity.

The disclosed technology can also appropriately combine the various embodiments described above with various modification examples. The disclosed technology is not limited to the above embodiments, and may adopt various configurations without departing from the gist. The disclosed technology extends to a storage medium for storing the program non-temporarily in addition to the program.

The contents described and illustrated above are detailed descriptions for the portions related to the disclosed technology, and are merely an example of the disclosed technology. For example, the above description of the configurations, functions, actions, and effects is an example of the configurations, functions, actions, and effects of the portions of the disclosed technology. Thus, the deletion of unnecessary portions, the addition of new elements, or the substitution may be performed for the contents described and illustrated above without departing from the gist of the disclosed technology. In order to avoid complications and facilitate understanding of the portions related to the disclosed technology, in the contents described and illustrated above, common technical knowledge that does not particularly require description is not described in order to enable the implementation of the disclosed technology.

In the present specification, "A and/or B" has the same meaning as "at least one of A or B". That is, "A and/or B" means that only A may be used, only B may be used, or a combination of A and B may be used. In the present specification, the same concept as "A and/or B" is also applied to a case where three or more matters are expressed by "and/or".

All the documents, patent applications, and technical standards described in the present specification are incorporated in the present specification by reference to the same extent as a case where individual documents, patent applications, and technical standards are specifically and individually noted to be incorporated by reference.

What is claimed is:

1. An information processing apparatus, comprising a processor that is configured to:
    acquire an output image output from a trained model as a result of causing the trained model to perform semantic segmentation in which discrimination of a class which is a type of an object appearing in an input image is performed on a pixel-by-pixel basis;
    evaluate validity of the semantic segmentation based on the output image; and
    perform control such that an evaluation result indicating that the semantic segmentation does not have validity is displayed in a case of evaluating that the semantic segmentation does not have validity,
    wherein the processor calculates an image feature value from the output image, and evaluates the validity of the semantic segmentation by using the image feature value, the image feature value being associated with a pre-selected image feature that is different from image features employed by the trained model that performs semantic segmentation.

2. The information processing apparatus according to claim 1,
    wherein the processor derive statistical information of the object appearing in the input image based on the output image, and
    perform control such that a warning indicating that reliability of the statistical information is low is displayed together with the evaluation result in a case of evaluating that the semantic segmentation does not have validity.

3. The information processing apparatus according to claim 1,
    wherein the processor perform control such that the output image evaluated as having no validity of the semantic segmentation is output.

4. The information processing apparatus according to claim 3,
    wherein the processor accept a correction instruction for the class of the output image evaluated as having no validity of the semantic segmentation.

5. The information processing apparatus according to claim 4,
    wherein the processor re-train the trained model by using, as learning data, a corrected output image obtained by correcting the class of the output image evaluated as having no validity of the semantic segmentation.

6. The information processing apparatus according to claim 3,
    wherein the processor correct the class of the output image evaluated as having no validity of the semantic segmentation.

7. The information processing apparatus according to claim 1,
    wherein the input image is a cell image obtained by imaging a plurality of cells in culture.

8. An information processing apparatus comprising a processor that is configured to:
    acquire an output image output from a trained model as a result of causing the trained model to perform semantic segmentation in which discrimination of a class which is a type of an object appearing in an input image is performed on a pixel-by-pixel basis;
    evaluate validity of the semantic segmentation based on the output image; and
    perform control such that an evaluation result indicating that the semantic segmentation does not have validity is displayed in a case of evaluating that the semantic segmentation does not have validity,
    wherein the processor calculates an image feature value from the output image, and evaluates the validity of the semantic segmentation by using the image feature value,
    wherein the input image is an image obtained by imaging one region of a plurality of regions obtained by dividing an imaging target, and
    wherein the processor generates an entire image indicating the entire imaging target by joining a plurality of the output images corresponding to a plurality of the input images imaged for the plurality of regions, and calculates, as the image feature value, an intensity of a periodic noise of the entire image which is caused by dividing the imaging target into the plurality of regions and imaging the divided regions.

9. An information processing apparatus comprising a processor that is configured to:
    acquire an output image output from a trained model as a result of causing the trained model to perform semantic segmentation in which discrimination of a class which is a type of an object appearing in an input image is performed on a pixel-by-pixel basis;
    evaluate validity of the semantic segmentation based on the output image; and
    perform control such that an evaluation result indicating that the semantic segmentation does not have validity is displayed in a case of evaluating that the semantic segmentation does not have validity,
    wherein the processor calculates an image feature value from the output image, and evaluates the validity of the semantic segmentation by using the image feature value,
    wherein the input image is a cell image obtained by imaging a plurality of cells in culture, and wherein the processor calculates, as the image feature value, an area ratio between at least two types of classes including the cell or a structure of the cell.

10. The information processing apparatus according to claim 9,
wherein the processor change a threshold value used for evaluating the validity of the semantic segmentation in comparison with the area ratio according to a type of the cell and/or the number of culture days of the cell.

11. A method for operating an information processing apparatus, comprising:
acquiring an output image output from a trained model as a result of causing the trained model to perform semantic segmentation in which discrimination of a class which is a type of an object appearing in an input image is performed on a pixel-by-pixel basis;
evaluating validity of the semantic segmentation based on the output image;
performing control such that an evaluation result indicating that the semantic segmentation does not have validity is displayed in a case of evaluating that the semantic segmentation does not have validity;
calculating an image feature value from the output image; and
evaluating the validity of the semantic segmentation by using the image feature value, the image feature value being associated with a pre-selected image feature that is different from image features employed by the trained model that performs semantic segmentation.

12. A non-transitory computer-readable storage medium storing an operating program of an information processing apparatus that is executable by a computer to:
acquire an output image output from a trained model as a result of causing the trained model to perform semantic segmentation in which discrimination of a class which is a type of an object appearing in an input image is performed on a pixel-by-pixel basis;
evaluate validity of the semantic segmentation based on the output image;
perform control such that an evaluation result indicating that the semantic segmentation does not have validity is displayed in a case of evaluating that the semantic segmentation does not have validity;
calculate an image feature value from the output image; and
evaluate the validity of the semantic segmentation by using the image feature value, the image feature value being associated with a pre-selected image feature that is different from image features employed by the trained model that performs semantic segmentation.

* * * * *